(12) United States Patent
Liang

(10) Patent No.: US 9,649,032 B2
(45) Date of Patent: May 16, 2017

(54) SYSTEMS AND METHODS FOR REMOTE MEASUREMENT OF THE EYES AND DELIVERING OF SUNGLASSES AND EYEGLASSES

(71) Applicant: Perfect Vision Technology (HK) Ltd., Tsuen Wan, N.T. (HK)

(72) Inventor: Junzhong Liang, Fremont, CA (US)

(73) Assignee: Perfect Vision Technology (HK) Ltd., Tsuen Wan, NT (HK)

( * ) Notice: Subject to any disclaimer, the term of this patent is extended or adjusted under 35 U.S.C. 154(b) by 57 days.

(21) Appl. No.: 14/646,734

(22) PCT Filed: Nov. 25, 2013

(86) PCT No.: PCT/US2013/071763
§ 371 (c)(1),
(2) Date: May 22, 2015

(87) PCT Pub. No.: WO2014/085352
PCT Pub. Date: Jun. 5, 2014

(65) Prior Publication Data
US 2015/0305619 A1    Oct. 29, 2015

Related U.S. Application Data

(63) Continuation-in-part of application No. 13/687,309, filed on Nov. 28, 2012, now Pat. No. 9,277,863.
(Continued)

(51) Int. Cl.
*A61B 3/14* (2006.01)
*A61B 3/18* (2006.01)
(Continued)

(52) U.S. Cl.
CPC .............. *A61B 3/18* (2013.01); *A61B 3/0025* (2013.01); *A61B 3/0033* (2013.01);
(Continued)

(58) Field of Classification Search
CPC .......... G02C 7/02; G02C 7/022; G02C 7/061; G02C 7/027; G02C 7/028; G02C 2202/22;
(Continued)

(56) References Cited

U.S. PATENT DOCUMENTS 2,021,812 A    11/1935 Scott
3,431,688 A     3/1969 Rudd et al.
(Continued)

FOREIGN PATENT DOCUMENTS

CN    2031935      2/1989
CN    1781443 A    6/2006
(Continued)

OTHER PUBLICATIONS

Notice of Allowance dated Apr. 12, 2016 for U.S. Appl. No. 14/465,755.
(Continued)

*Primary Examiner* — Mahidere Sahle
(74) *Attorney, Agent, or Firm* — The Mueller Law Office, P.C.

(57) ABSTRACT

The present disclosure provides methods, devices, and systems for automated measured correction of the eyes and provision of sunglasses and eyeglasses for individuals, including individuals with a visual acuity of 20/20 or better. Methods, devices and systems for remote measurement of refraction by an examiner away from the measurement system are also disclosed.

6 Claims, 18 Drawing Sheets

Related U.S. Application Data which is a continuation-in-part of application No. 13/116,262, filed on May 26, 2011, now Pat. No. 8,419,185, which is a continuation of application No. PCT/US2009/066148, filed on Nov. 30, 2009.

(60) Provisional application No. 61/200,494, filed on Dec. 1, 2008, provisional application No. 61/208,045, filed on Feb. 20, 2009.

(51) Int. Cl.
| | | |
|---|---|---|
| *A61B 3/036* | (2006.01) | |
| *A61B 3/00* | (2006.01) | |
| *A61B 3/028* | (2006.01) | |
| *A61B 3/10* | (2006.01) | |
| *A61B 3/15* | (2006.01) | |
| *G06F 19/00* | (2011.01) | |
| *G02C 7/02* | (2006.01) | |

(52) U.S. Cl.
CPC .......... *A61B 3/0058* (2013.01); *A61B 3/0083* (2013.01); *A61B 3/0285* (2013.01); *A61B 3/036* (2013.01); *A61B 3/1015* (2013.01); *A61B 3/152* (2013.01); *G02C 7/02* (2013.01); *G06F 19/321* (2013.01); *G06F 19/322* (2013.01); *G02C 2202/22* (2013.01)

(58) Field of Classification Search
CPC ... G02C 13/003; A61B 3/1015; A61B 3/0285; A61B 3/032; A61B 3/103
USPC ................. 351/169, 176, 208–218
See application file for complete search history.

(56) References Cited

U.S. PATENT DOCUMENTS

| | | | |
|---|---|---|---|
| 5,434,707 A | 7/1995 | Dalzell et al. | |
| 5,652,638 A | 7/1997 | Roffman et al. | |
| 5,777,719 A | 7/1998 | Williams et al. | |
| 6,108,634 A | 8/2000 | Podnar et al. | |
| 6,142,625 A | 11/2000 | Sawano et al. | |
| 8,214,265 B2 | 7/2012 | Peters | |
| 8,219,466 B2 | 7/2012 | Gui et al. | |
| 8,229,806 B1 | 7/2012 | Chapman et al. | |
| 8,235,247 B2 | 8/2012 | Alvarez | |
| 8,276,735 B2 | 10/2012 | Georgens | |
| 8,419,185 B2 | 4/2013 | Liang | |
| 8,820,931 B2 * | 9/2014 | Walsh ............... | A61B 3/102 351/206 |
| 2004/0054358 A1 | 3/2004 | Cox et al. | |
| 2004/0263786 A1 | 12/2004 | Williams et al. | |
| 2005/0174535 A1 | 8/2005 | Lai et al. | |
| 2005/0200809 A1 | 9/2005 | Dreher et al. | |
| 2006/0023163 A1 | 2/2006 | Foster | |
| 2006/0203198 A1 | 9/2006 | Liang | |
| 2006/0235369 A1 | 10/2006 | MacRae et al. | |
| 2006/0279699 A1 | 12/2006 | Liang | |
| 2007/0118428 A1 * | 5/2007 | Akiyama ............. | A61B 3/10 351/206 |
| 2007/0159593 A1 | 7/2007 | Hibino et al. | |
| 2008/0018855 A1 | 1/2008 | Larichev et al. | |
| 2008/0126809 A1 | 5/2008 | Rothschild | |
| 2008/0143960 A1 | 6/2008 | MacRae | |
| 2008/0143963 A1 | 6/2008 | Lindacher | |
| 2009/0128901 A1 | 5/2009 | Tilleman et al. | |
| 2009/0244480 A1 | 10/2009 | De Gaudemaris et al. | |
| 2009/0323020 A1 | 12/2009 | Zhao et al. | |
| 2010/0074477 A1 | 3/2010 | Fujii et al. | |
| 2010/0283963 A1 | 11/2010 | Giraudet et al. | |
| 2011/0228225 A1 | 9/2011 | Liang | |
| 2012/0057124 A1 | 3/2012 | Spivey et al. | |
| 2012/0253837 A1 | 10/2012 | Cashman et al. | |
| 2012/0271412 A1 | 10/2012 | Feingold et al. | |
| 2013/0100410 A1 | 4/2013 | Liang | |

FOREIGN PATENT DOCUMENTS

| | | |
|---|---|---|
| EP | 0857455 A2 | 8/1998 |
| GB | 1463107 A | 2/1977 |
| JP | 554131950 | 10/1979 |
| JP | 3601604 A | 1/1985 |
| JP | H03229212 | 10/1991 |
| JP | H05332720 A | 12/1993 |
| JP | H06034920 | 2/1994 |
| JP | H0915541 A | 1/1997 |
| JP | H10175149 A | 6/1998 |
| JP | 11056779 A | 3/1999 |
| JP | H11267100 A | 10/1999 |
| JP | H11295668 | 10/1999 |
| JP | 2002156611 | 5/2002 |
| JP | 2003140094 | 5/2003 |
| JP | 2006178245 A | 7/2006 |
| JP | 2006517135 A | 7/2006 |
| JP | 2007240553 A | 9/2007 |
| JP | 2009521726 A | 6/2009 |
| WO | 2005040896 A1 | 5/2005 |
| WO | 2007075975 A2 | 7/2007 |
| WO | 2008049503 A2 | 5/2008 |
| WO | 2009123700 A | 10/2009 |
| WO | 2010065475 A | 6/2010 |
| WO | 2012054651 A2 | 4/2012 |

OTHER PUBLICATIONS

Office Action dated Feb. 3, 2016 for U.S. Appl. No. 14/465,755.
Extended European Search Report Dated May 3, 2016 for European Patent Application No. 13857854.7.
Office Action dated Jun. 21, 2016 for Japanese Patent Application No. 2011-538720.
Extended European Search report dated May 13, 2014 for EP Aplication No. 09830937.0.
International Search Report and Written Opinion dated Nov. 28, 2013 for PCT Application No. PCT/IB2013/001051.
International Search Report and Written Opinion dated Apr. 9, 2014 for PCT Patent Application No. PCT/US2013/071763.
International Search Report and Written Opinion dated Jun. 25, 2010 for PCT Application No. PCT/US2009/066148.
Japanese Office Action dated Oct. 29, 2013 for JP Application No. 2011-538720.
Notice of Allowance dated Feb. 22, 2013 for U.S. Appl. No. 13/116,262.
Notice of Allowance dated May 12, 2014 for U.S. Appl. No. 13/682,527.
Office Action dated Apr. 3, 2015 for U.S. Appl. No. 13/687,309.
Office Action dated Aug. 16, 2012 for U.S. Appl. No. 13/116,262.
Office action dated May 13, 2014 for Japanese Application No. 2011-538720.
Office Action dated Sep. 19, 2013 for U.S. Appl. No. 13/682,527.
Pretrial ReExamination Report dated Nov. 28, 2014 for Japanese Patent Application No. 2011-538720.
Notice of Allowance dated Nov. 3, 2015 for U.S. Appl. No. 13/687,309.
Office Action dated Nov. 10, 2015 for Japanese patent application No. 2011-538720.
Office Action dated Sep. 30, 2015 for U.S. Appl. No. 14/465,755.
Extended European Search Report dated Jul. 5, 2016 for European Patent Application No. 13859414.8.

* cited by examiner

Misaligned     Eye aligned to the Phoroptor     Phoroptor aligned to the Eye

SYSTEMS AND METHODS FOR REMOTE MEASUREMENT OF THE EYES AND DELIVERING OF SUNGLASSES AND EYEGLASSES

CROSS-REFERENCE TO RELATED APPLICATIONS

This application claims priority to International Application No. PCT/US2013/071763 entitled "Systems and Methods for Remote Measurement of the Eyes and Delivering of Sunglasses and Eyeglasses" filed Nov. 25, 2013 and published as International Publication No. WO 2014/085352; which is a continuation-in-part of U.S. patent application Ser. No. 13/687,309 entitled "Methods and Systems for Automated Measurement of the Eyes and Delivering of Sunglasses and Eyeglasses" filed on Nov. 28, 2012; which is a continuation-in-part of U.S. patent application Ser. No. 13/116,262 entitled "Methods and Devices for Refractive Correction of the Eyes" filed May 26, 2011 and issued on Apr. 16, 2013 as U.S. Pat. No. 8,419,185; which is a continuation of International PCT Application No. PCT/US09/66148, filed Nov. 30, 2009; which claims the benefit of U.S. Provisional Patent Application No. 61/200,494, filed Dec. 1, 2008 and the benefit of U.S. Provisional Patent Application No. 61/208,045 filed Feb. 20, 2009; and all of which are incorporated herein by reference.

BACKGROUND

Refractive corrections for human eyes can be characterized into two general categories. The first category is the conventional method of vision correction which corrects for the eye's focus error and cylindrical error as measured using a manifest refraction. The second category is wavefront-guide vision correction which provides correction for all aberrations in an eye, including focus error, cylindrical error, spherical aberration, coma, and others, measured using an objective wavefront sensor.

The conventional method of vision correction is conceptually limited to a correction of just focus error and cylindrical error. In addition, it is also constrained by the subjective nature of how the manifest refraction determines the eye's refractive errors, particularly the eye's cylindrical error. Cylindrical error is also known as astigmatism, and it causes particular problems because it includes both a cylindrical power and a cylindrical axis.

There are at least five limiting factors associated with a manifest refraction. First, manifest refraction is limited by available lenses in a phoroptor because a manifest refraction relies on applying corrective lenses and testing vision of the eye subjectively. Focus error is usually limited to a resolution of 0.125 Diopters (D) while the cylindrical error is limited to a resolution of 0.25 D. Second, subjective determination of cylindrical axis can be problematic because a slight variation of cylindrical axis—within only a few degrees—can cause a significant performance difference for a cylindrical correction of more than 2 D. Third, human errors by either the patient or a practitioner such as an optometrist or optician cannot be excluded because a manifest refraction involves the subjective responses of a patient to a plurality of refractive corrections, as well as the practitioner's analysis of those subjective responses. Fourth, a manifest refraction is fundamentally a partial empirical refractive solution, because a practitioner conducting the manifest refraction determines an end point for a refractive correction in a time-consuming process. Finally, manifest refraction can also be a time consuming process because it relies on human control of vision optimization with as many as three independent variables which include a focus error, a cylindrical power, and a cylindrical axis.

The drawbacks associated with using a manifest refraction compound with the high tolerance of current lens manufacturing techniques and lead to widespread erroneous vision correction. The inaccuracy of the conventional vision correction method using a manifest refraction leads to a situation where there may be significant differences in a refractive prescription of the same eye by different practitioners, as well as in a coarse resolution of cylindrical power—as large as 0.25 D—universally prescribed for conventional vision correction. Consequently, available ophthalmic lenses in today's ophthalmic industry are also limited to lenses in 0.25 D resolution. Correcting an eye's astigmatism using conventional vision correction is further complicated by the high tolerance in fabricating conventional spectacle lenses. Moreover, it is accepted in the industry that visual acuity of 20/20 is perfect already with no need for correction.

SUMMARY

In one aspect of the invention, an automated method for determining a refractive correction of an eye is provided.

Thus, certain embodiments of the present invention provide methods for providing a pair of sunglasses to an individual, including individuals with a visual acuity of 20/20 or better, comprising the steps of: 1) providing a measuring station configured for automatic data acquisition without necessary intervention from a human other than the individual, the measuring station configured to obtain an objective measurement of wave aberration from each eye of the individual; place a plurality of lenses according to the obtained an objective measurement of wave aberrations into a correction module for the individual to see through and to read at least one acuity chart; and determine a focus power of each eye through subjective refraction, wherein the subjective refraction involves subjective responses from the individual to a plurality of focus powers; 2) generating correction data for making the pair of sunglasses; 3) transmitting data for making the pair of sunglasses via an electronic media, wherein the transmitted data contains at least the correction data for making the pair of sunglasses; 4) manufacturing lenses for the sunglasses based on the correction data; 5) fitting the lenses into frames to produce finished sunglasses; and 6) providing the finished pair of sunglasses to the individual.

In some aspects of this embodiment, the pair of sunglasses provided is an over-the-counter pair of sunglasses that does not require a prescription. In some aspects, the measuring station further is configured to accept results from the individual in reading the acuity-chart through the correction module for each eye, and in some aspects the measuring station further is configured to allow the individual to manually adjust the focus power of the correction device. In some aspects, the transmitting data step for making the pair of sunglasses further includes at least one of following for reviewing and checking by a human other than the individual: a) records for the obtained an objective measurement of wave aberration from each eye of the individual, b) results of the individual in reading the acuity chart through the correction device for a plurality of focus powers.

In some aspects of this embodiment of the invention, the measuring station further is configured to determine a measured cylindrical power and cylindrical axis from the objective measurement of wave aberration. In some aspects, the measuring station further is configured to offer to and receive from the individual a selection of sunglass frames in some aspects, the generated correction data for lenses is modified to take into account of the shape of selected sunglass frames, and in some aspects, the measuring station further is configured to take a picture of the individual with and/or without the selected pair of sunglasses.

In some aspects of the invention, the measuring station further is configured to accept payment information from the individual, and in some aspects, the measuring station further is configured to accept delivery information from the individual.

In some aspects of the invention, the measuring station further is in communication with a lens fabricator and is configured to transfer the correction data to a lens fabricator to manufacture custom lenses, and in some aspects, the lens fabricator is automated. Further, in certain aspects, the measuring station is in communication with the automated lens fabricator and is configured to transfer the correction data and delivery information from the individual to a lens fabricator to manufacture custom lenses, and in some aspects, the measuring station further is configured to offer to and receive from the individual selected sunglass frame styles.

In some aspects of this method of the invention, the automated lens fabricator is further configured to assemble the manufactured custom lenses with the selected sunglass frames, and in some aspects of this embodiment, the measuring station further is configured to accept payment information and delivery information from the individual.

In yet other aspects, the lens fabricator is not automated. In other aspects, based on the correction data for each eye, off-the-shelf lenses are selected for the individual. In other aspects, the lenses are manufactured by molding or by machining.

In yet other aspects of this embodiment, the measuring station comprises a wavefront phoroptor for measuring refractive corrections of a focus error and a cylinder error for an eye, where the wavefront phoroptor comprises: a wavefront sensing module for providing the objective measurement of aberrations of the eye, measuring wavefront slopes across a pupil, and determining wave aberration of the eye that includes at least a cylindrical axis and a cylindrical power in a resolution finer than 0.25 D; and a phoroptor module with a plurality of spherical lenses and cylindrical lenses and an acuity chart for subjectively determining the focus error of the eye. In some aspects, the cylindrical lenses are set according to the objective measurement of aberrations from the wavefront sensing module; where the subjectively determined focus error involves subjective responses by the individual to a plurality of focus powers by the eye viewing an acuity chart, and in some aspects, the wavefront sensing module measures aberrations of the eye using a lenslet array wavefront sensor. In yet other aspects, the objective measurement further includes a focus error, a spherical aberration, a coma and other high-order aberrations, and wherein the cylinder power and the cylinder angle is determined for optimized vision from the determined wave aberration across a pupil of the eye.

Yet other embodiments of the present invention provide a measuring station configured for automatic data acquisition without necessary intervention from a human other than the individual configured to: obtain an objective measurement of wave aberration from each eye of the individual; determine a measured cylindrical power and a cylindrical axis from the objective measurement of wave aberration; place a plurality of lenses according to the determined measured cylindrical power and a cylindrical axis into a correction module for the individual to see through and read an acuity chart; determine a focus power of each eye through subjective refraction, where the subjective refraction involves subjective responses from the individual to a plurality of focus power corrections; and communicate the measured cylindrical power, cylindrical axis and focus power of each eye to a lens fabricator to manufacture custom lenses or to a repository of off-the-shelf lenses.

Aspects of this embodiment of the invention include the measuring station configured further to accept results from the individual in reading the acuity chart through the correction module and/or the measuring station further configured to allow the individual to manually adjust the focus power of the correction module. In other aspects, the measuring station further is configured to transmit data for review by a human other than the individual, wherein the transmitted data includes at least one of a) records for the obtained objective measurement of wave aberration from each eye of the individual, and b) results of the individual in reading the acuity chart through the correction device for a plurality of focus powers, and in some aspects, the measuring station further is configured to take a picture of the individual.

Other embodiments of the invention provide a system for providing a pair of sunglasses to an individual, including individuals with a visual acuity of 20/20 or better, comprising: a measuring station configured for automatic data acquisition without necessary intervention from a human other than the individual obtain an objective measurement of wave aberration from each eye of the individual and determine a measured cylindrical power and a cylindrical axis from the objective measurement of wave aberration; place a plurality of lenses according to the determined cylindrical power and cylindrical axis into a correction module for the individual to see through and read an acuity chart; and determine a focus power of each eye through subjective refraction, wherein the subjective refraction involves subjective responses from the individual from a plurality of focus powers; and a lens fabricator to manufacture custom lenses or a lens repository to provide off-the-shelf lenses according to the measured cylindrical power, cylindrical axis and focus power. In some aspects, the system further comprises a database configured to receive payment and delivery information from the individual.

Other embodiments of the invention provide a method for providing a pair of sunglasses to an individual, including individuals with a visual acuity of 20/20 or better, comprising the steps of: 1) providing a measuring station to the individual, the measuring station configured to automatically and without input from a human other than the individual: obtain an objective measurement of wave aberration from each eye of the individual; determine a measured cylindrical power and a cylindrical axis from the objective measurement of wave aberration; place a plurality of lenses according to the determined cylindrical power and a cylindrical axis from the objective measurement of wave aberration into a correction device for the individual to see through and read an acuity chart; and determine a focus power of each eye through subjective refraction, wherein the subjective refraction involves subjective responses from the individual to a plurality of refractive corrections; 2) generating correction data from which to manufacture lenses; 3) manufacturing the lenses or selecting a set of off-the-shelf lenses appropriate for the correction data; 4) fitting the lenses into frames to produce finished sunglasses; and 5) providing the finished sunglasses to the individual.

Yet other embodiments of the present invention provide a kiosk system for prescriptive sunglasses or eyeglasses, configured for automatic data acquisition without necessary intervention from a human other than the individual, comprising: a wavefront sensing module for providing objective measurement of aberrations of the eye, wherein the wavefront sensing module measures wavefront slopes across a pupil and determines wave aberration of the eye that includes at least a cylindrical axis, and a cylindrical power in a resolution finer than 0.25 D; a vision correction module for presenting a plurality of refractive corrections for the individual to see through, wherein the plurality of refractive corrections includes: a cylindrical power and a cylindrical axis according to the determined wave aberrations, and a plurality of focus power corrections that is controlled manually by the individual; an acuity chart for determining visual acuity of the eye under the plurality of focus power corrections, human-to-machine interface module to accept results from the individual in reading the acuity chart through the correction module for a plurality of focus power corrections; an exporting module for communicating data to a lens fabricator to manufacture custom lenses or to a repository of off-the-shelf lenses, wherein the communicated data includes at one of the following: the measured cylindrical power, cylindrical axis and focus power of each eye; records of the wavefront module for data review; and results of the individual in reading the acuity chart through the correction device for a plurality of focus power corrections.

In another embodiment of the invention, a method of manufacture for producing an ophthalmic lens is provided, including automated methods of manufacture. In a first step, correction data including wavefront aberration and focus power lens is transmitted by a measuring station to a lens fabricator and is received by the lens fabricator. In a second step, a semi-finished blank is selected by the lens fabricator. In a third step, the semi-finished blank is placed in a lens surfacing system in the lens fabricator. In a fourth step, the surface of the semi-finished blank is surfaced based on the correction data received from the measuring station and a set of known refractive properties of the semi-finished blank to create a fabricated lens. In a fifth step, the refractive power of the fabricated lens is measured with a lensometer to determine the refractive error between the refractive power and the correction data. In a final optional step, the surface of the fabricated lens is reworked based on the determined refractive error until a measured cylindrical power of the fabricated lens and the cylindrical power of the correction data are within a tolerance of between 0.01 D and 0.08 D.

Various objects, features, aspects and advantages of the present invention will become more apparent from the following detailed description of preferred embodiments of the invention.

DETAILED DESCRIPTION OF THE EMBODIMENTS

Figure 1A:
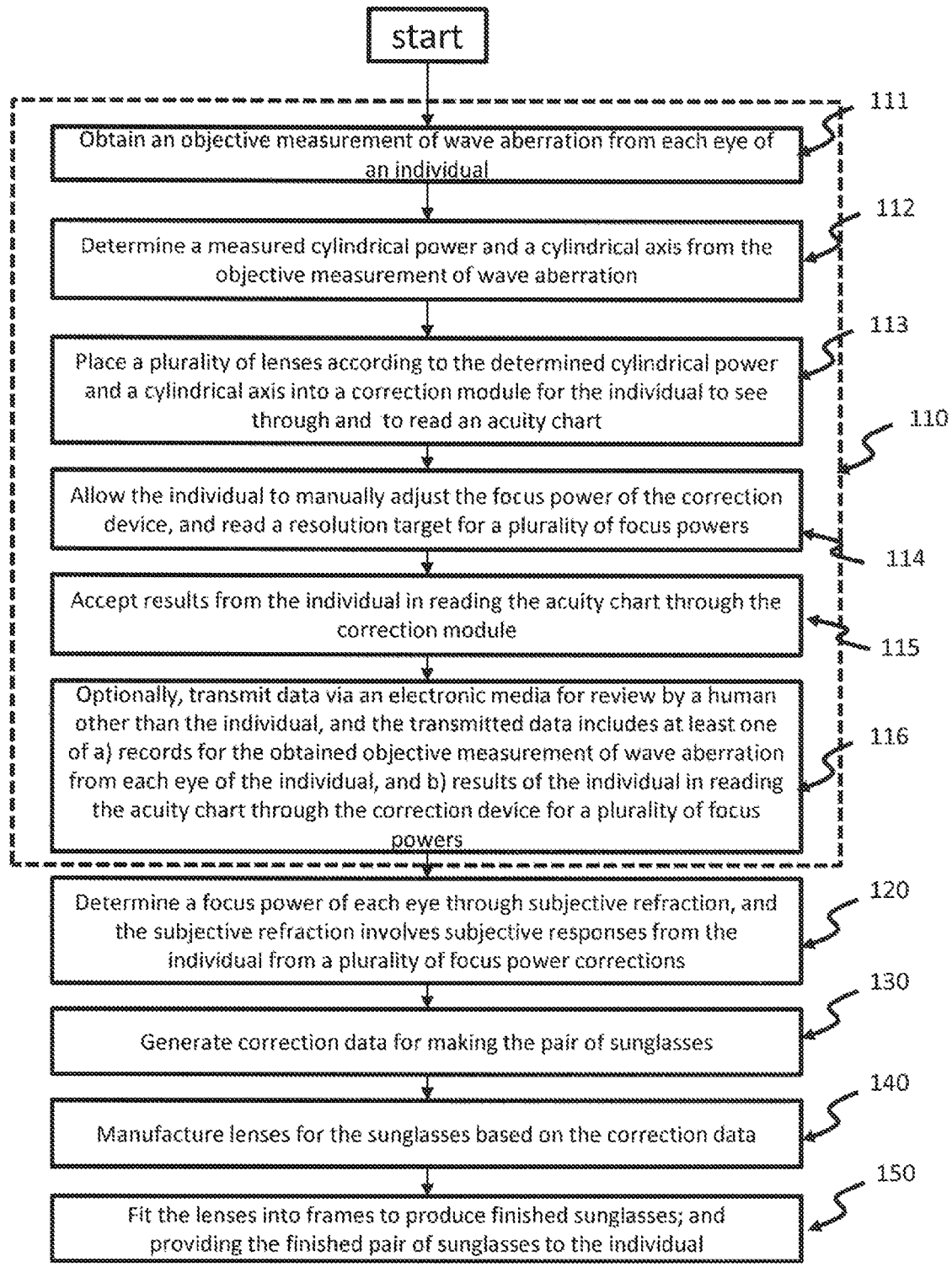
FIG. 1a shows a flow chart for a method for automated measured correction of the eye and provision of sun- or eye-glasses in accordance with one embodiment.

Reference now will be made in detail to embodiments of the present disclosure, one or more examples of which are illustrated in the accompanying drawings. Each example is provided by way of explanation of the present technology, not as a limitation of the present technology. In fact, it will be apparent to those skilled in the art that modifications and variations can be made in the present technology without departing from the scope thereof. For instance, features illustrated or described as part of one embodiment may be used with another embodiment to yield a still further embodiment. Thus, it is intended that the present subject matter covers such modifications and variations as come within the scope of the appended claims and their equivalents.

The present disclosure is drawn to refraction systems for remote measurement of refractive errors in the eye in a location such as a shop or office, by an examiner situated away from the location. The remote measurement occurs through a network connection such as internet, for example to enable electronic commerce (e-commerce). Methods are disclosed for delivering eyeglasses through remote measurement of refractive errors in human eyes, and methods for franchise stores for eyeglasses.

Automated Measurement of the Eyes

The present disclosure is drawn to automated methods, devices and systems to provide sunglasses and eyeglasses that allow for vision correction, even for individuals with visual acuity of 20/20 or better. The present disclosure particularly is revolutionary because it provides sunglasses for vision correction of emmetropic eyes, when very typically sunglasses are sold "off-the-shelf" with lenses that offer no optical correction. Though sunglasses most typically do not offer refractive correction, sunglasses are important as they offer protection from UV rays, and protection from eye discomfort due to bright light. Current sunglasses also typically offer options such as polarization for glare reduction, and various lens colors such as brown for enhanced depth perception and grey for color fidelity. The present disclosure is applicable for frames of any shape, and particularly applicable to sunglasses (or goggles) that have wrap shapes, since for such configurations, correction of vision is important because the lens is not parallel to the cornea. Thus, in contrast to the conventional approach to selling sunglasses, the present disclosure is drawn to automated methods, devices and systems that provide sunglasses that allow for enhanced vision correction, even in individuals that have a visual acuity of 20/20 or better or in individuals who wear contact lenses for vision correction.

Emmetropia is defined as the state of vision where an object at infinity is in sharp focus with the eye lens in a neutral or relaxed state. This condition of the normal eye is achieved when the refractive power of the cornea as well as the crystalline lens and the axial length of the eye balance out, which focuses rays exactly on the retina of the eye, resulting in perfect vision. An eye in a state of emmetropia requires no correction; however, emmetropic eyes actually are not perfect. For example, FIGS. 2 and 3 demonstrate that there are optical defects for emmetropic eyes between 20/20 and 20/10. Further, sunglasses provide additional challenges for emmetropes. For example, the reduced light level due to the darkened lenses can cause problems, as can the transition from bright light to clouded or overcast conditions.

Moreover, the inventor has collected additional clinical data indicating that astigmatism (cylinder error) in eyes with an acuity of 20/10 or 20/12 can be as large as 0.60 D in some eyes as measured by a wavefront aberrometer; and that correcting an eye's astigmatism in 20/10 and 20/12 eyes showed significant medical benefits for sunglasses. It was found that both brightness and contrast improved as did depth perception. The inventor also has collected more clinical data in individuals with an acuity of 20/25, 20/20, or 20/16 showing that both focus error and cylinder error (astigmatism) are important. Astigmatism in eyes with a visual acuity of 20/25, 20/20, or 20/16 can be as large as 1.0 D in some eyes, as measured by a wavefront aberrometer; and that correcting an eye's focus error and astigmatism in eyes with a visual acuity of 20/25, 20/20, or 20/16 can improve visual acuity by 2 to 4 lines, and brightness, contrast and depth perception are improved.

FIG. 1*a* shows a flow chart for a method for automated measured correction of the eye and provision of sun- or eye-glasses to an individual in accordance with one embodiment. First, a measuring station or kiosk 110 is provided. The measuring station or kiosk preferably comprises: 1) a comfortable place for the individual to sit; 2) a wavefront sensing module for providing objective measurement of aberrations of the eye; where the wavefront sensing module measures wavefront slopes across a pupil and determines wave aberration of the eye that includes at least a cylindrical axis, and a cylindrical power in a resolution finer than 0.25 D; 3 a vision correction module for presenting a plurality of refractive corrections for the individual to see through, where the plurality of refractive corrections includes a cylindrical power and a cylindrical axis according to the determined wave aberrations, and a plurality of focus powers that are controlled manually by the individual; 4) an acuity chart for determining visual acuity of the eye under the plurality of focus power corrections; 5) a human-to-machine input module for the individual to communicate with the measuring station, to accept results from the individual in reading the acuity chart through the correction module for a plurality of focus power corrections, and, optionally, to accept delivery information from the individual; 6) an exporting module for communicating data to a lens fabricator to manufacture custom lenses or to a repository of off-the-shelf lenses, where the communicated data includes at least one of the following: the measured cylindrical power, cylindrical axis and focus power of each eye; records of the wavefront module for data review; or results from the individual reading the acuity chart through the correction device for a plurality of focus power corrections; 7) optionally, an image module for taking a picture of the individual with and/or without the selected sunglass frames; and 8) optionally, an electronic payment module for accepting payment information from the individual.

The measuring station 110 is configured to: 1) automatically acquire data without intervention from a human other than the individual, by obtaining an objective measurement of wave aberration from each eye of the individual 111; 2) determine a measured cylindrical power and a cylindrical axis from the objective measurement of wave aberration 112; 3) place a plurality of lenses according to the determined cylindrical power and a cylindrical axis into a correction module for the individual to see through and read an acuity chart 113; 4) allow the individual to manually adjust the focus power of the correction device and read a resolution target for a plurality of focus powers 114; 5) accept results from the individual in reading the acuity chart through the correction module 115; and 6) optionally, transmit data via an electronic media for review by a human other than the individual 116, where the transmitted data includes at least one of a) records for the obtained objective measurement of wave aberration from each eye of the individual, and b) results of the individual in reading the acuity chart through the correction device for a plurality of focus powers.

Additionally, the measuring station 110 is configured to determine a focus power of each eye through subjective refraction, where the subjective refraction involves the measuring station receiving subjective responses from the individual to a plurality of focus powers 120.

The measuring station of the present disclosure determines focus power under a cylindrical correction according to wavefront measurements. Cylinder power and cylinder axis both have an impact on subjective focus power. The advantages of determining cylinder power and cylinder axis according to wavefront measurements include eliminating the two independent knobs typically used in the art to measure subjective refraction. This provides state-of-the-art quality of vision after correction as the eye is astigmatism-free according to objective measurement of the eye's wave aberration. Focus power must be determined subjectively because the eye can accommodate for different focuses, ensuring perfect focus power avoiding overcorrection and undercorrection.

The automated measuring station of the present disclosure provides many advantages described above, and provides additional advantages. Traditional refractive correction requires subjective refraction for at least three parameters: focus power, cylinder power and cylinder angle, and these parameters are most often measured by a professional such as an optometrist or an optician. The measurements taken are often complicated because traditional instruments have three independent knobs for vision optimization—thus, such measurements and instrumentation cannot be automated. However, the methods and devices of the present can be automated because cylinder angle and cylinder axis are precisely determined objectively via a wavefront aberrometer. It is well-known that conventional auto-refractions cannot distinguish image blurs caused by focus error, cylinder error (cylinder power & cylinder axis), spherical aberration coma and a host of other high-order aberrations in the eye. When human vision is optimized in a conventional auto-refractor for the sharpest image possible, determination of the eye's cylinder power and cylinder angle is impacted by the real-time focus error (the eye's accommodation) as well as the eye's other aberrations: spherical aberration and coma. Unlike conventional auto-refractors, a wavefront aberrometer measures all aberrations in an eye independently through a wavefront sensor. Measurement of the eye's cylinder power and cylinder axis is thus not influenced by the eye's real-time focus error such as accommodation or by spherical aberration, coma, and many other high-order aberrations. A wavefront aberrometer provides cylinder angle and cylinder power with unprecedented precision, so that they can be used as the final cylinder power and cylinder axis without the need of subjective validation as in the conventional manifest refraction. Additionally, focus power of any eye must be subjectively determined as the eye must accommodate for different distances, refraction of the eye requires only one knob, which can be manipulated by the individual patient at the measuring station.

The wavefront sensor that is part of the measuring station of the present disclosure can be run automatically on command, and unlike a conventional auto-refractor, it can provide wavefront sensor images for independent review so that wavefront measurement can be validated later by an individual such as a optical professional, if desired. When an automatic measurement of eye's cylinder power and cylinder angle is used for fabricating a correction lens, it is preferred in some embodiments to have an independent validation by a human other than the tested individual. Wavefront images and their analysis provide direct evidence for another individual to determine whether the automatic measurement of the cylinder angle and the cylinder power are acceptable. Conventional autorefractors do not have the necessary information for an independent validation. Additionally, for the validation and determination of focus power of the eye, it is preferred that another individual review subjective acuity for a plurality of focus powers. Otherwise, because the eye can accommodate to different focus powers, focus power determined by the tested individual based on best visual acuity alone can lead to overcorrection leading to hyperopia of the eye. In some embodiments, the methods further comprise allowing a human other than the tested individual to review data transmitted from the measuring station and to allow the individual to send feedback data remotely to the measuring station to correct any errors in or fine tune the automatic measurements.

The measuring station of the present disclosure may also provide additional functionalities. For example, the measuring station may present to the individual a selection (different styles and/or sizes and/or colors) of sun- or eyeglass frames for consideration, either physical samples or virtual samples. In addition, the measuring station may take a digital photograph of the individual so that the individuals can "virtually" try on different frame styles, sizes and colors, with the digital images provided to the individual by the measuring station. Moreover, the digital images provided may serve a purpose aside from aesthetics and fashion; for example, another advantage of taking a photograph is as glasses frames are positioned on an individual's face, the lenses will be positioned in relation to the eye—more or less uniquely depending on the individual's face and the frames selected. Taking a photograph of the individual's face in combination with information about the frame style and size selected allows software associated with the measuring station to optimize alignment of the optical center of the lens with the individual's eye's pupils. Other functionalities that may be associated with the measuring station include the measuring station accepting payment from the individual, accepting prescription information for an individual (to provide vision correction in accordance with a prescription with, e.g., additional vision correction as determined by the methods of the present disclosure), accepting delivery (e.g., shipping) information from an individual, and accepting a focus power for near vision of an individual with presbyopia so that the sunglasses can be made as bi-focal, tri-focal, and progressive lenses.

In another step of FIG. 1a, correction data based on the measured wave aberrations and focus power (correction data) is generated by the measurement station 110, or by a computer in communication with the measurement station. In another step, the correction data 130 (along with other data such as digital image, prescription, payment, delivery and/or any other pertinent data) is then transmitted from the measurement station (or computer in communication with the measurement station) via electronic media to a lens fabricator.

The lens fabricator may be a manual lens fabricator or may be an automated lens fabricator. Descriptions of lens fabrication are provided herein in the section entitled "High-precision toric lenses for refractive corrections" and in conjunction with the description of FIG. 5. Essentially, lenses are manufactured by molding or machining or a combination of the two 140. For example, semi-finished lens blanks are "generic" lenses that provide a certain range of correction, and then are typically custom finished to precise specifications based on the correction data (or prescription) for the individual. The present disclosure contemplates transmitting data to an automated, a semi-automated or a manual lens fabricator, where lenses are manufactured based at least on the correction data transmitted by the measurement station to the lens fabricator. In addition to fabricating the lenses, the lens fabricator may also fit the lenses into the frames of the sun- or eyeglasses 150. Finally, the finished sun- or eyeglasses are provided to the individual 150. As with the manufacturing step and the fitting step, providing the finished sun- or eyeglasses to the individual may be an automated process, a semi-automated process, or a manual process based on, e.g., delivery information provided by the individual, input into the measurement station or otherwise provided by the individual.

Improved Methods for Determining a Refractive Correction of an Eye

Figure 1B:
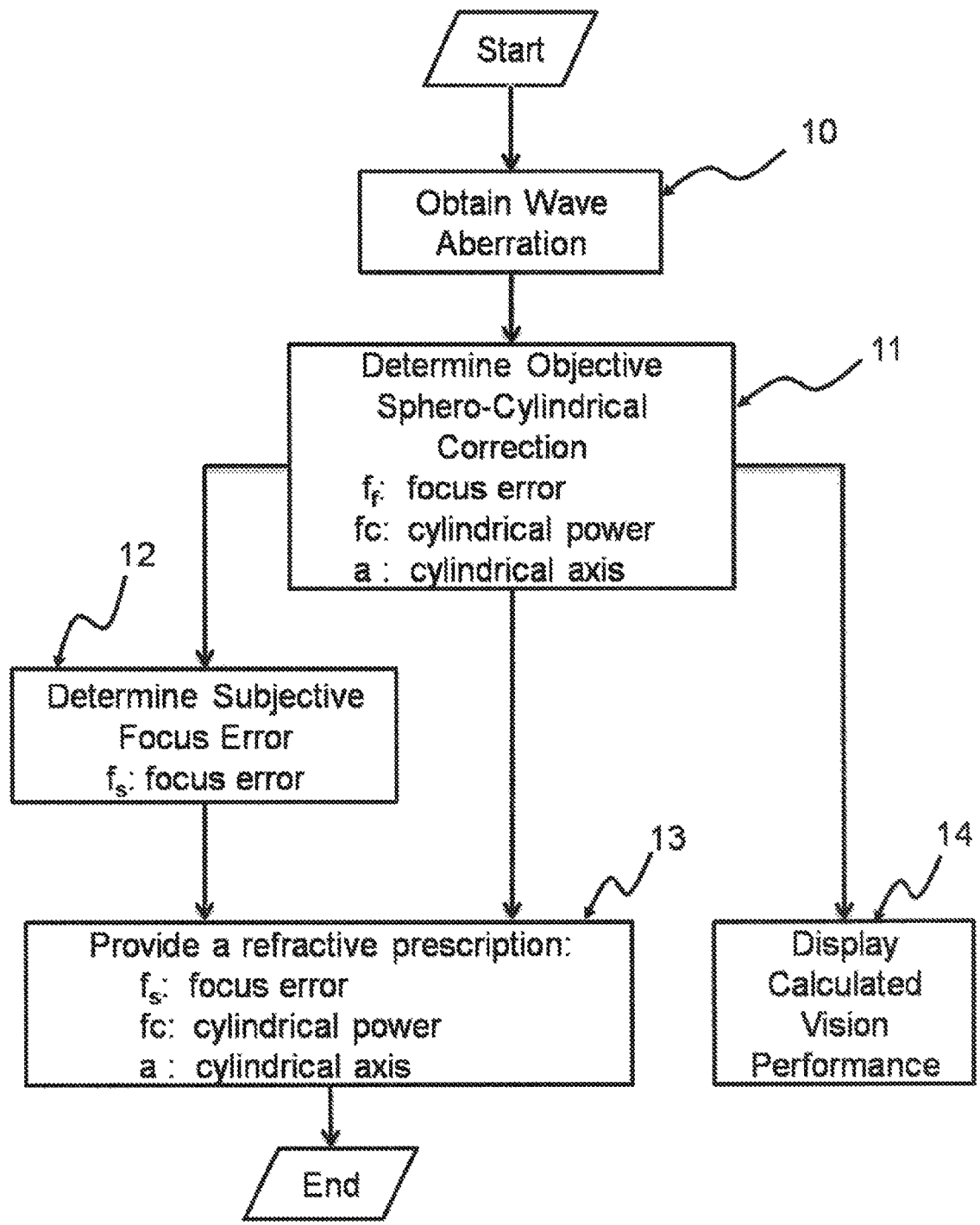
FIG. 1b shows a flow chart for a method for determining a refractive correction of an eye that is in accordance with an embodiment.

FIG. 1b shows a flow chart for an improved method for determining a refractive correction of an eye based on an objective measurement of the eye's wave aberration and a subjective measurement of the eye's focus error in accordance with steps 111, 112 and 120 of FIG. 1a. This improved method enables the production of an optimized astigmatism-free refractive correction so that a majority of normal human eyes can achieve visual acuity of 20/10 instead of conventional 20/20 and provides even individuals with a visual acuity of 20/10 with corrected, enhanced vision.

First, in step 10, an objective measurement of all the aberrations in an eye is obtained, wherein all aberrations are expressed in a wave aberration $W(x,y)$. Second, in step 11, an objective sphero-cylindrical correction is determined from the obtained wave aberration by optimizing vision of the eye through removal of measured focus errors and cylindrical errors. The objective sphero-cylindrical correction comprises a focus error, a cylindrical power, and a cylindrical axis. Third, in step 12, a focus error of the eye is obtained through a subjective refraction, wherein the subjective refraction involves measuring vision performance of an eye based on subjective responses to a plurality of refractive corrections. Finally, in step 13, refractive correction data for an ophthalmic lens or refractive procedure is generated by combining the objectively determined cylindrical power, the objectively determined cylindrical axis, and the subjectively determined focus error.

The method described has many advantages in comparison to conventional vision correction. First, cylindrical error in an eye as little as 0.025 D can be precisely determined just like other high-order aberrations such as spherical aberration and coma in an eye, because the refraction process does not depend on the limited cylindrical lenses in a phoroptor, subjective feedback about the fine difference between different cylindrical corrections by the tested subjects, and subjective optimization strategies used by the practitioners. Second, the cylindrical axis can be precisely determined and a tolerance for an error in cylindrical axis can be determined from the calculated image quality of an eye. Finally, vision optimization is no longer limited to a specific situation in a manifest refraction. Instead, virtual optimization can be applied to take account of different conditions of vision at different pupil sizes through the use of vision simulation of outdoor vision, indoor vision, and night vision.

In contrast to the objective wavefront refraction using a wavefront aberrometer as described in U.S. Pat. No. 5,777,719 by Williams and Liang, the method described also addresses the issue of measuring focus error in the eye using an objective refraction. Objective wavefront sensors like a wavefront aberrometer can measure focus error accurately, but cannot guarantee that the measured focus error is the best for far vision of an eye for two reasons. First, human eyes are known to change focus power by the crystalline lens at different viewing distances, which is also called accommodation. An objective wavefront sensor can only measure the focus error of an eye at one particular accommodation state. Second, objective wavefront sensors like an objective aberrometer only measure focus error of an eye at one particular wavelength of light, which is often in the infrared spectrum to assure the patient remains comfortable during the objective refraction. Chromatic aberration for perception must be taken into account for determining the best focus for an eye for the far accommodation point. Therefore, the focus error obtained from an objective refractor could be the true focus error for the far accommodation point within +0.125 D for only about 20% of measured eyes.

About 40% of eyes will be under-corrected based on the focus error derived from an objective refractor, which will lead to a visual acuity below 20/20. At the same time, another 40% will be over-corrected based on the focus error obtained from an objective refractor, which leads to hyperopic vision after the refractive correction. The improved method for determining a refractive correction discussed here in accordance with the present disclosure uses a subjective approach to revise the focus error from the objective refractor, and thus takes into account both accommodation and chromatic aberration for an optimized refraction of the eye's far accommodation point.

The described improved method for determining a refractive correction can further include a preview of vision correction, as in step 14, even before an ophthalmic lens is made. Prediction of vision may include convolved retinal images of acuity charts, calculated modulation transfer functions, calculated point-spread functions, and simulation of nighttime symptoms. The calculated vision performance can be shown to a patient as well as a practitioner for accepting or selecting a specific refractive correction.

Figure 2:
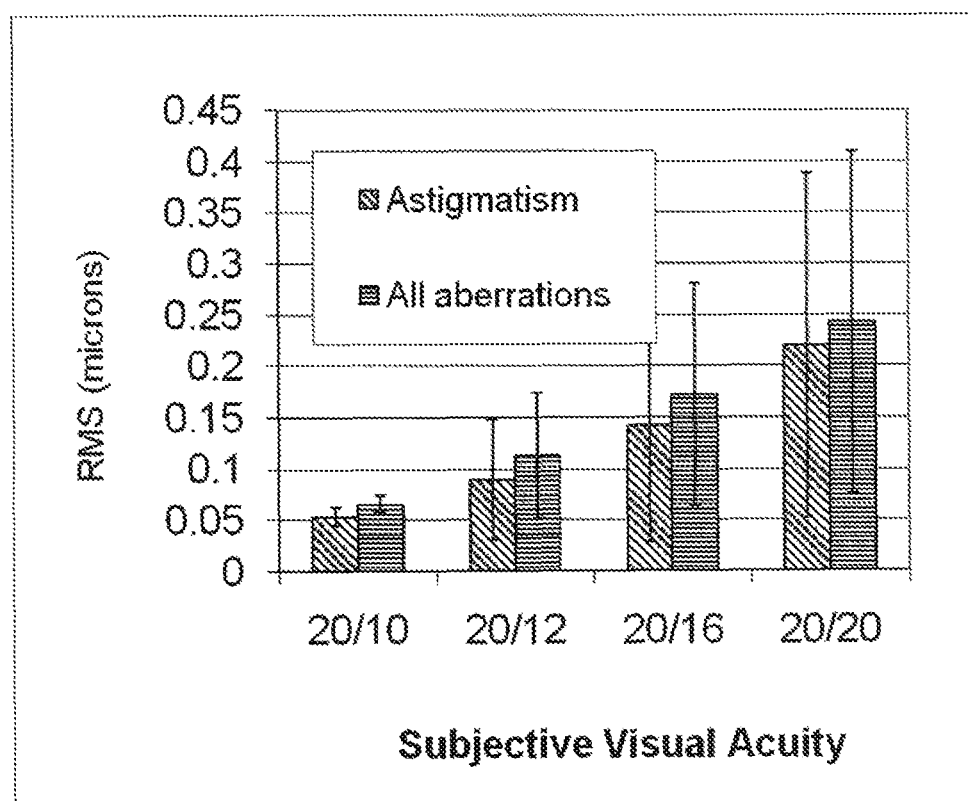
FIG. 2 shows aberrations in emmetropic eyes having subjective visual acuity better than 20/20 without any refractive correction.

The described improved method for determining a refractive correction enables an optimized astigmatism-free refraction for every eye. Perfect correction of an eye's cylindrical error can have significant impact on the visual acuity of a corrected eye. FIG. 2 shows the cylindrical error as well as the total aberration in more than 200 eyes with visual acuity better than 20/20. All the tested eyes are naturally emmetropic without any refractive correction. The cylindrical error and total aberrations in each eye are measured with an objective wavefront sensor and calculated based on the pupil size for each eye during the subjective measurement of visual acuity. The pupil size of acuity measurements ranges between 2.5 Min and 4.5 mm with an average pupil size of 3.7 mm. The error bars in FIG. 2 is one standard deviation for the measured population.

As can be seen in FIG. 2, the objectively measured cylindrical error and the subjectively measured acuity are correlated. In addition, it is clear that the cylindrical error is the dominant factor in determining subjective visual acuity.

Figure 3:
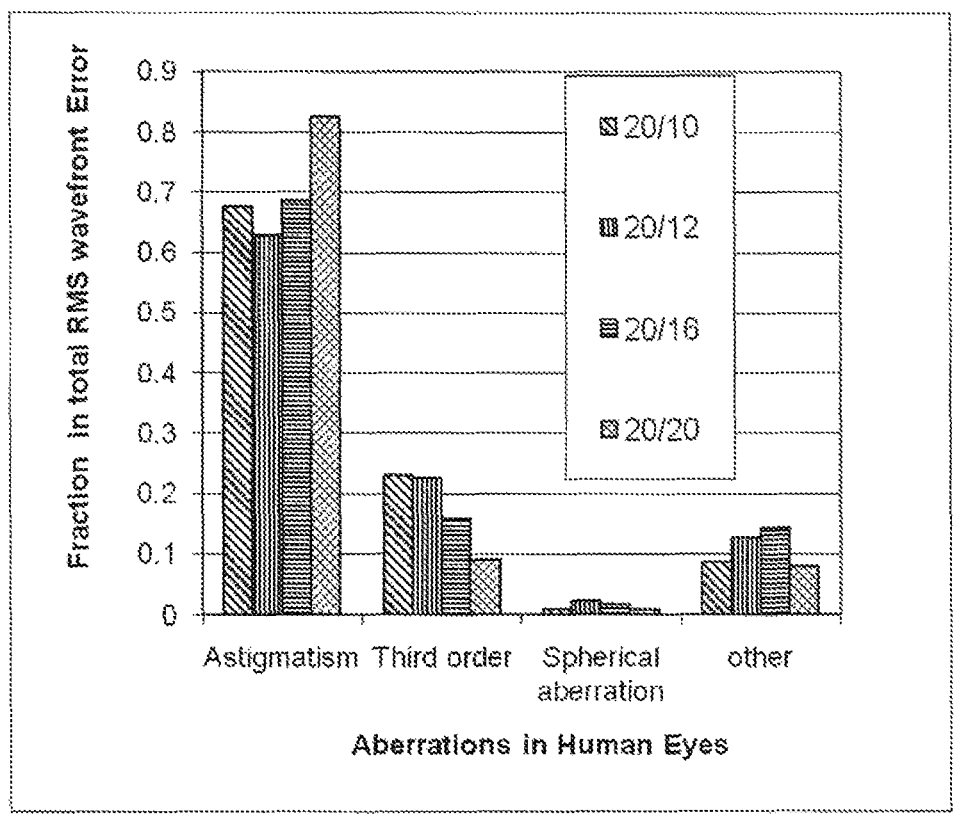
FIG. 3 shows fractions of different aberrations in the total aberration for emmetropic eyes having visual acuity better than 20/20 without any refractive correction.

FIG. 3 also highlights the importance of cylindrical error for visual acuity in naturally emmetropic eyes. FIG. 3 shows averaged fractions of different aberrations in the total aberrations for emmetropic, eyes in four acuity groups in a yet to be published clinical study. It is seen that the cylindrical error accounts for 60% to 80% of all aberrations in emmetropic eyes in an acuity test. Coma has a much smaller contribution of 10% to 20%, while spherical aberration has negligible impact on visual acuity.

From the data in FIG. 2 and FIG. 3, it is not difficult to conclude that quality in correcting the cylindrical error in an eye has significant impact on subjective visual acuity. Visual acuity of 20/10 or 20/12 can usually be achieved just by a perfect correction of cylindrical error. Although important for vision at nighttime, additional correction of coma, spherical aberration, and other high-order aberrations has negligible impact on visual acuity for the majority of normal human eyes.

Perfect correction of an eye's cylindrical error requires precise measurements and specification of the cylindrical error in an eye. It is therefore necessary to specify cylindrical power much finer than the conventional resolution of 0.25 D, e.g. 0.025 D.

It is also important to record cylindrical axis in the objective measurement. One embodiment for recording the cylindrical axis is to record a digital picture of an eye while the objective measurement of cylindrical error is taken. The digital picture can later be used to assist the placement of an ophthalmic lens in an eye, or to verify proper orientation of an ophthalmic lens.

The described method for determining a refractive correction, when combined with innovations also described in the present application for advanced lens making, will enable an astigmatism free customized refractive correction that is superior in visual performance to the conventional method for vision correction based on conventional manifest refraction.

In one embodiment of the present disclosure, a method for obtaining an astigmatism-free customized refractive correction comprises the steps as follows. First, a wave aberration of an eye is obtaining objectively, wherein the wave aberration includes focus error, astigmatism, coma, and spherical aberration in the eye. Obtaining a wave aberration of an eye objectively can be achieved by measuring wave aberration of an eye using a device like an objective aberrometer as described in in U.S. Pat. No. 5,777,719 by Williams and Liang. Second, a cylindrical power and a cylindrical axis are determined from the objectively obtained wave aberration. The resolution for the cylindrical power must be finer than 0.25 D, e.g., 0.025 D. The specification for the determined cylindrical power has a resolution between 0.01 D to 0.1 D. Cylindrical axis must also be precisely determined. Third, a focus power of the eye is determined through subjective refraction. Subjective refraction can be achieved through the use of a phoroptor presented by the measuring station or kiosk to the individual patient. Fourth, a refractive prescription for an ophthalmic lens or for a refractive procedure is generated by combining the objectively determined cylindrical power and cylindrical axis, and the subjectively determined focus power. Fifth, a pre-made lens most closely correlating to the determined cylindrical power, cylindrical axis and focus power is selected from a stock of such lenses or a customized ophthalmic lens is fabricated based on the generated high-precision refractive correction data with a high-precision cylindrical power. In preferred embodiments, the cylindrical power has a resolution finer than 0.25 D, e.g., 0.025 D, with a tolerance between 0.01 D and 0.05 D. Additionally, the refractive correction can further include a spherical aberration that is determined from the wave aberration. Reducing spherical aberration in some eyes can improve night vision, particularly for those eyes with known nighttime symptoms such as glare and halo.

Figure 4:
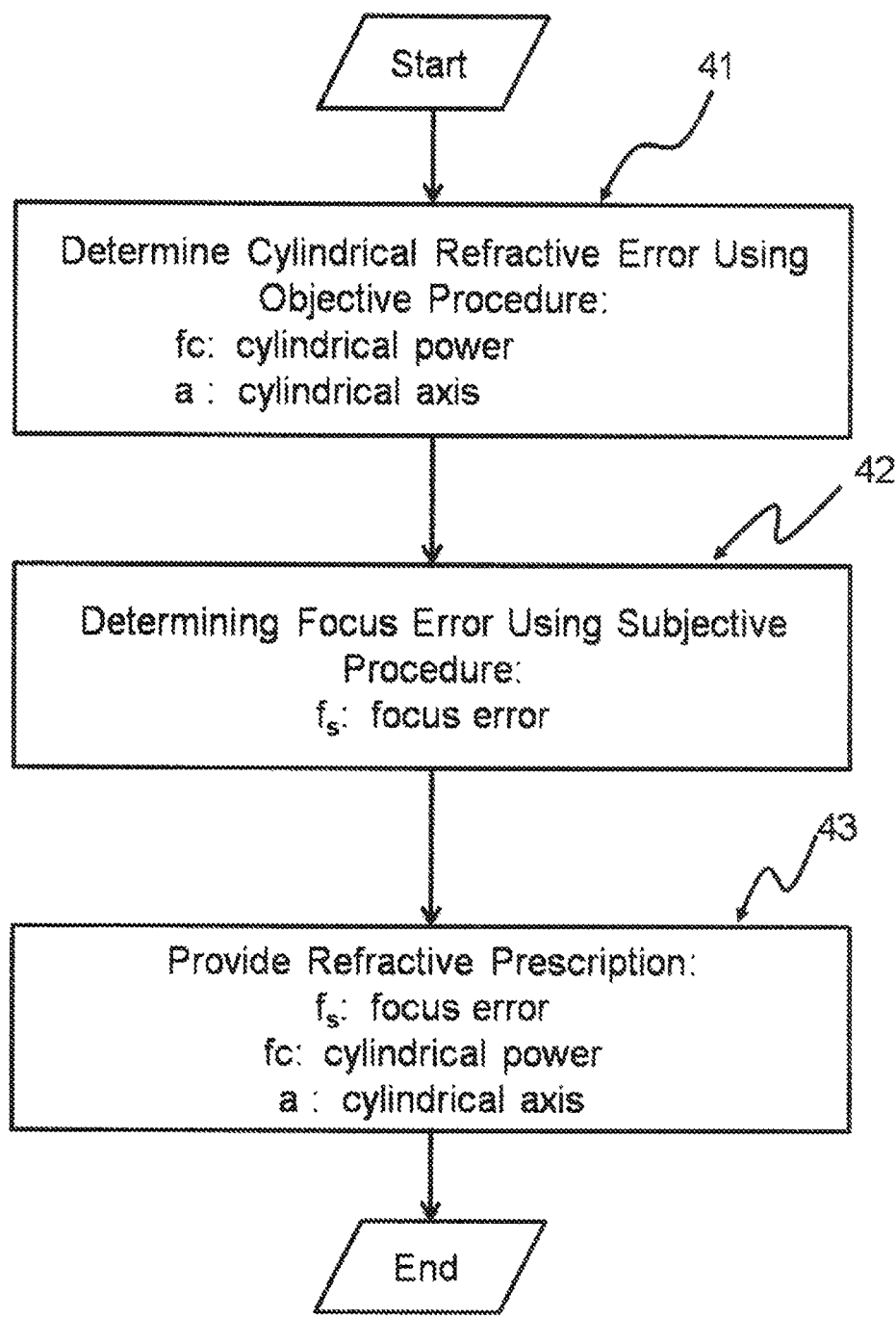
FIG. 4 shows a flow chart for a method for determining refractive correction of an eye in accordance with an embodiment.

In another embodiment of FIG. 1b, a simplified method for a perfect correction of eye's cylindrical error is shown in FIG. 4. This embodiment does not involve measuring high-order aberrations such as spherical aberration and coma. First, in step 41, a cylindrical error of an eye is determined using an objective procedure without any subjective responses. For improved accuracy in determining the cylindrical error, the objective procedure in step 41 might involve measuring refractive properties of an eye in a pupil size between 2.5 mm and 4 mm pupil, and taking an average measurement for a plurality of independent objective measurements. Second, in step 42, a focus error of the eye is determined through a subjective refraction measuring vision performance of an eye based on subjective responses to a plurality of refractive corrections. Third, in step 43, correction data used to select or manufacture an ophthalmic lens is generated by combining the determined cylindrical refractive error and determined focus error, wherein the cylindrical error has a finer resolution less than the traditional 0.25 D, e.g., 0.025 D.

High-Precision Toric Lenses for Refractive Corrections

Due to the limitations in the conventional manifest refraction, ophthalmic lenses today are made with a cylindrical power resolution of 0.25 D. Corrections of astigmatism in human eyes using real spectacle lenses is further complicated because lenses are in reality made with a relative large tolerance of between +0.09 D for low power lenses and up to +0.37 D for high power lenses. Therefore, spectacle lenses for astigmatism-free customized refractive corrections must be made using more advanced technologies.

FIG. 1a provides a step to manufacture lenses based on the correction data generated and transmitted by the measuring station. Spectacle lenses today are made using either: lens molding or lens machining using computer-controlled lathes. For the majority of spectacle lenses in a normal refraction range (spherical power between −6 D and +6 D), lenses are typically molded in batches, and stocked either in labs or in lens shops. Two lens molds are needed, and one mold has a base curve that is either spherical or aspheric in shape and the other mold has a toric shape if the spectacle lens has a cylindrical power. For lenses with a refractive power beyond the normal range, lenses are usually fabricated from semi-finished lens blanks that are molded in batches and stocked in factories. A semi-finished lens blank contains a finished base surface in a spherical or aspheric curve and a top prescription or machinable surface that will be surfaced based on the lens prescription and optical power of the base surface. If the fabricated lens has a cylindrical power, the top surface will have a toric shape.

For both molded lenses and machined lenses with a cylindrical power, the finished lenses consists of a base curve that is spherical or aspheric in shape, and a prescription or machinable curve that is toric in shape for a custom lens with a cylindrical power. The base curve is often set to one of 5 to 8 possible surface shapes, while the prescription or machinable surface must be capable of taking on the shape of one of several hundred curves in order for the combined lens to correct for different combination of spherical and cylindrical powers with the conventional resolution of 0.25 D.

For spectacle lenses with a fine cylinder resolution of 0.025 D instead of 0.25 D, manufacturers would need ten times more prescription curves if they continued to use the conventional lens shape with one toric surface. Although possible in theory, making custom lens for astigmatism-free correction using one toric surface would be prohibitively expensive because of the enormous number of molds that would be needed.

Figure 5:
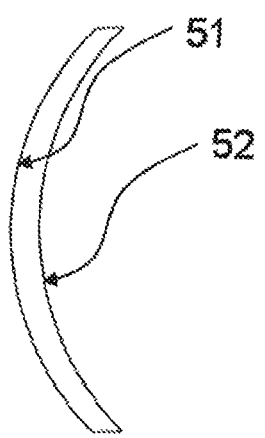
FIG. 5 shows an ophthalmic lens in accordance with an embodiment.

FIG. 5 illustrates new spectacle lenses in accordance with the present disclosure for astigmatism-free customized refractive correction. In one embodiment of the present disclosure, the lens comprises a toric surface 51 that is a modified version of traditional base curves used in conventional lenses. A small amount of cylindrical power (<0.25 D) can be added to a traditional base curve for fine tuning cylindrical power at a resolution below 0.25 D. The other toric surface 52 can be the same as those used in making conventional toric lenses, which have cylindrical powers ranging from 0.00 D to 6.00 D with a resolution of 0.25 D. Both the base curve and the prescription or machinable curve can also have aspheric characteristics for reducing oblique astigmatism just like conventional toric lenses.

Two embodiments can be used for fine tuning cylindrical powers as fine as 0.025 D. One of the embodiments involves a fixed cylindrical power of 0.25 D or 0.125 D at the base curve, adjusting the angle between the two cylinder axes, and thereby achieving cylindrical power resolution as fine as 0.025 D. The other embodiment involves a plurality of cylindrical powers for each base curve (0.025 D, 0.05 D, 0.075 D, 0.10 D, 0.125 D, and 0.2 D), combining the cylindrical power from the base curve and the prescription curve, and thereby achieving fine cylindrical power as fine as 0.025 D. In the second embodiment, axes of the two toric surfaces can be made to coincide to achieve the designed cylindrical powers, or slightly different for further tuning of cylindrical powers.

For manufacturing lenses with two toric surfaces that both have cylindrical powers, it is important to control orientations of the two cylinder axes to achieve a desired cylindrical power. When a spectacle lens is molded with two toric molds, each mold can have a machine-readable mark. Two molds should be aligned on their cylinder axes before being put together to form a cavity for molding a lens. When a lens is machined for two toric surfaces, the semi-finished blanks can contain a machine readable mark to indicate the cylindrical axis of the finished surface. The cylindrical axis of the machined surface should be precisely controlled in reference to the axis of the pre-finished surface.

In another embodiment, the ophthalmic lens in FIG. 5 can be further configured to induce spherical aberration at the central vision for the correction of spherical aberration in an eye. This can be achieved by shaping one of the two toric surfaces with an aspheric component around optical axis.

The ophthalmic lens of in FIG. 5 can further be configured to have aspheric shapes away from the optical axis for reduced off-axis Seidel aberrations. It can also be configured for a bi-focal lens or a progressive lens.

Controlling Cylindrical Power by Arranging Cylinder Axes of Toric Surfaces

Cylindrical powers in a fine resolution can be achieved by arranging the cylinder axes of two toric surfaces with coarse powers. In accordance with the present disclosure, the method requires two toric surfaces, where one of the two surfaces has a dominant cylindrical power in one direction $\Phi_{A1}$ while the other surface has a small biasing cylindrical power at a different orientation $\Phi_{A2}$. The angle between the two cylinder axes is measured by.

The combined cylindrical power can be expressed by an analytical expression:

$$A = \mathrm{SQRT}(A_1 * A_1 + A_2 A_2 + 2 * A_1 A_2 * \mathrm{COS}(2)) \qquad (1)$$

where SQRT is the mathematic operator of square root. The combined cylindrical power $\Phi A$ is between $(\Phi_{A1}-\Phi_{A2})$ and $(\Phi_{A1}+\Phi_2)$, depending on the angle between the two cylinder axes. In one example, if the dominant cylindrical power $\Phi_{A1}$ has a cylindrical power of 1.0 D and the bias cylindrical power is 0.125 D, any cylindrical power in a fine resolution between 0.875 D and 1.125 D can obtained using these two base cylindrical powers. In another example, a base bias cylindrical power of 0.25 D and 12 base dominant cylindrical powers of 0.25 D, 0.75 D, 1.25 D, 1.75 D, 2.25 D, 2.75 D, 3.25 D, 3.75 D, 4.25 D, 4.75 D, 5.25 D, 5.75 D, is used to achieve any cylindrical power between 0.00 D and 6.00 D with a resolution finer than 0.25 D.

There are at least three advantages associated with making a lens with a cylindrical power using two cylinder elements arranged at different cylinder axes. First, a high-resolution, adjustable cylindrical power can be achieved by arranging the relative orientation of the two cylinder axes. Controlling two cylinder axes within 2.5 degree is relatively easy in a manufacture process in comparison to a precise control of surface shape within 0.02 D. Second, making cylinder lenses in a fine resolution of cylindrical power is dramatically simplified and is low-cost because only a limited number of base molds are required. Third, a high-speed process can be achieved by fabricating all lenses with one bias power or just a few biasing cylindrical powers. High-definition lenses can then be custom manufactured just like a conventional lens with a limited number of cylindrical powers. One only needs to pay attention to the relative angle between the two cylinder axes.

It must be mentioned that arranging two cylindrical powers at various orientations will cause a variable focus offset to the base spherical power. The induced spherical power can be expressed as $$s = 0.5 * (A_1 + A_2 - A) \qquad (2)$$

where $\Phi_{A1}$, $\Phi_{A2}$ and $\Phi A$ are the dominate cylindrical power, the biasing cylindrical power and the combined cylindrical power, respectively. The total focus change depends on the angles between the two cylindrical axes, and can be as large as the biasing cylindrical power if the full range of angle between the two cylinder axes is 90 degrees. Because of the focus offset, this cylinder control method cannot be used for making conventional lenses with a resolution of 0.25 D.

When the bias cylindrical power is less than 0.25 D, the focus change in spectacle lenses can be addressed in two different ways. First, for eyes with significant accommodation range, the focus change in Eq (2) can be factored into the total spherical power. Second, for eyes with no or little accommodation, more than one bias power is needed to reduce the induced focus offset in Eq. (2). In this case, one may need five to ten bias powers and use a small angular range for fine tuning the combined cylindrical power.

In addition to making lenses with precise control of cylindrical power, the method of arranging two cylindrical powers described has three other applications. First, precise control of cylindrical power can be achieved even if the bias cylindrical power and the dominant cylinder are known to have manufacturing errors. A compensation angle can be calculated for eliminating the errors in the bias and dominant cylindrical powers. Second, one can use the principle described to build an improved phoroptor for preview of astigmatism-free custom vision corrections. Third, this method can also be used for making customized intra-ocular lenses.

Closed-Loop Methods for Making Customized High-Precision Toric Lenses

Customized spectacles for astigmatism-free refractive correction cannot be manufactured in today's labs using existing technologies because today's spectacle lenses are manufactured in a coarse resolution of 0.25 D and a rough tolerance between +0.09 D to +0.37 D as illustrated in British standard for tolerances on optical properties of mounted spectacle lenses (BS 2738-1:1998). Novel methods are required for making high-precision lenses for an astigmatism-free customized refractive correction.

A method for fabricating a customized toric lens for the high-definition refractive correction of a human eye in accordance with the present disclosure would utilize a closed-loop process. First, a manufacturer would receive custom correction data for the manufacture of a toric lens with a spherical power, and a cylindrical power in a finer resolution than 0.25 D, e.g., 0.025 D. Second, desired surface profiles for a lens would be determined based on the obtained refractive correction data and the material used for making the ophthalmic lens. Third, a customized toric lens would be fabricated either through lens molding or by surfacing a semi-finished blank based on the determined surface profiles. Fourth, each fabricated custom lens would be measured with a lensometer. The lens would be delivered to a customer only if the measured cylindrical power of the manufactured lens and the cylindrical power of the manufactured lens were within a custom tolerance level between 0.01 D and 0.08 D, e.g., 0.025 D. The lens would be reworked by surfacing at least one of the two surfaces if the difference between the measured cylindrical power of the manufactured lens and the cylindrical power measured by the measuring station is not within a custom tolerance level.

In another embodiment of the present disclosure, the closed loop process for making a high-precision spectacle lens comprises the steps of: a) obtaining correction data (in some embodiments, a prescription) that comprises a spherical focus power, a cylindrical power, and an optional cylindrical axis and spherical aberration; b) determining desired surface profiles for a lens based on the obtained refractive prescription and the material used for making the ophthalmic lens; c) mounting a component in the form of an optical piece or a partially processed optical element into a manufacture system and altering at least one surface profile of the component according to the determined surface profiles; d) measuring refractive properties of the altered component using a lensometer; f) calculating residual errors of the manufactured lens from the obtained correction data and the measured refractive data of the altered component; e) further changing at least one surface profile of the component based on the calculated residual errors until the residual errors of the manufactured lens are within a custom tolerance between 0.01 D and 0.08 D, e.g., 0.025 D.

Methods for Previewing an Astigmatism-Free Refractive Correction

Even though objective wavefront refractors provide precise measurements of cylindrical power and cylindrical axis of an eye, it is still preferred to preview the cylinder correction before a lens is made for the cylindrical correction.

A phoroptor is a device normally used in an optometry office for the subjective determination of a spherical focus power, a cylindrical power, and a cylindrical axis of an eye. Differences in cylindrical powers for a refractive correction are limited by a resolution of 0.25 D while differences in cylindrical axis are set by a resolution of about 5 degrees. Cylindrical axes in a phoroptor are never precisely related to an objective refraction in optometry practice. Therefore, conventional phoroptors in the prior art are not suited for high-definition refractive correction.

Figure 6:
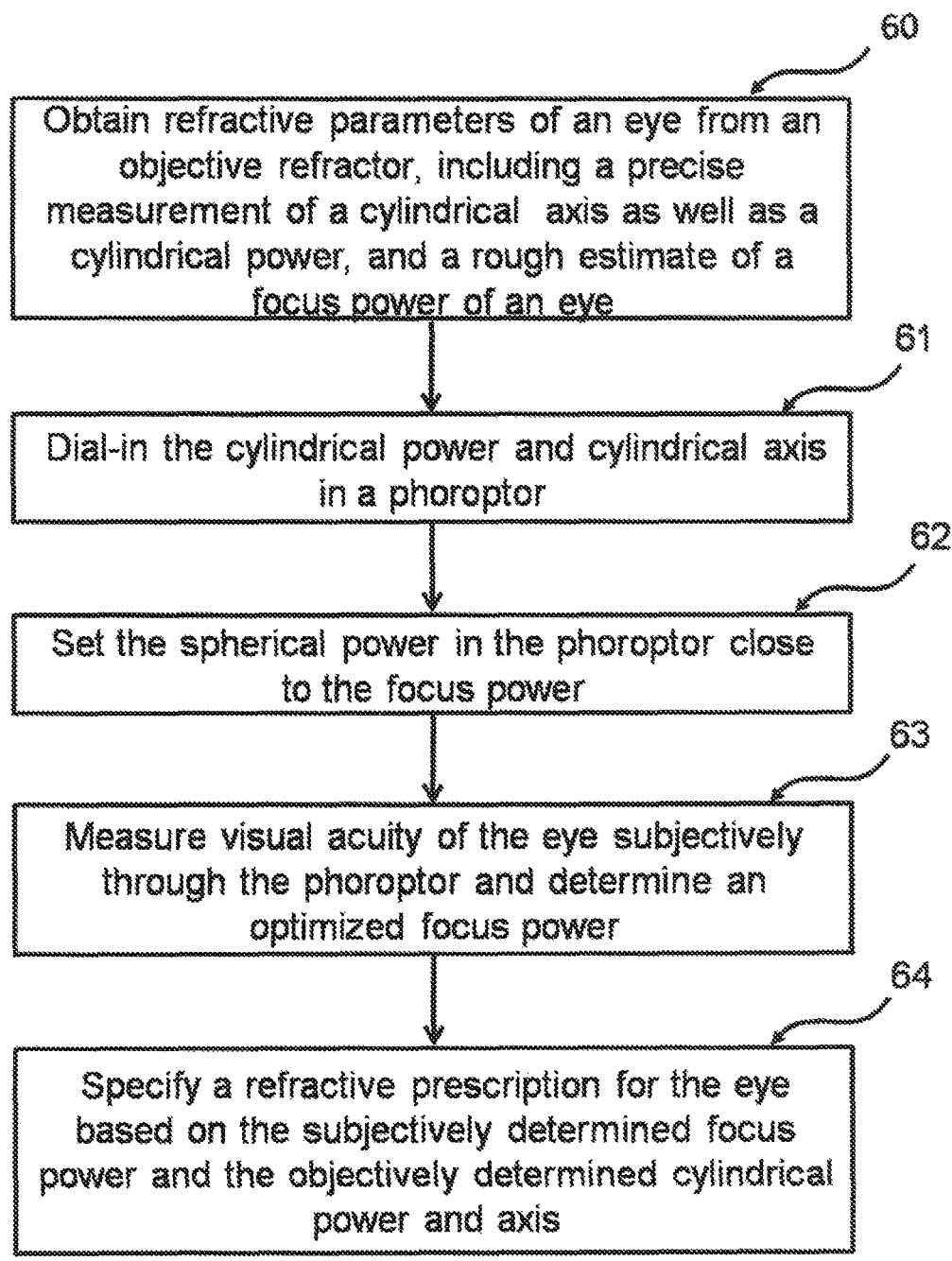
FIG. 6 shows a method for previewing a refractive correction of an eye in accordance with an embodiment.

FIG. 6 shows a method for previewing an astigmatism-free refractive correction of an eye in accordance with the present invention. In one embodiment, the method for previewing an astigmatism-free refractive correction of an eye in accordance with the present invention comprises the steps of: a) obtaining correction data of a refractive correction of an eye from an objective refractor 60, wherein the objective refractor measures wavefront slopes across the pupil of an eye, and precisely determines a cylindrical power (at a resolution finer than 0.25 D), a cylindrical axis, an optional spherical aberration, and a rough estimate of a spherical focus power of an eye; h) dialing-in the determined cylindrical power and cylindrical axis in a phoroptor 61, wherein the cylinder parameters are controlled precisely with a resolution finer than 0.25 D; c) setting the spherical focus power to a plurality of values and measure visual acuity of an eye subjectively through phoroptor 62; d) determining an optimized focus power subjectively that sets the eye's accommodation at the far point 63; e) determining the best corrected acuity under preview and provide a refractive prescription 64 based on the subjectively determined focus power and the objectively determined cylindrical power and cylindrical axis.

Improved Phoroptors for Measuring Refractive Errors of an Eye

The method of previewing an astigmatism-free refractive correction in accordance with the method described above may be achieved using a phoroptor equipped with a wavefront aberrometer. In one embodiment, such an advanced phoroptor would comprise the following modules: a wavefront sensing module for providing an instant and objective measurement of an eye's aberrations; an output module for displaying the measured aberrations that include at least a focus error, a cylindrical axis and a cylindrical power in a resolution finer than 0.25 D, e.g., 0.025 D; a mechanical mechanism for moving the wavefront aberrometer to a position for measuring the eye's aberrations as well as for moving the wavefront aberrometer away from the optical axis of the eye for other measurements of the eye, a phoroptor module for performing subjective refraction of an eye using a plurality of spherical lenses and cylindrical lenses, wherein the phoroptor module may not correct high-order aberrations such as spherical aberration and coma; and a mechanism in the phoroptor module for dialing in a cylindrical power and cylindrical axis obtained from the output device of the wavefront aberrometer so that an astigmatism-free vision correction is achieved. The wavefront module would also measures all aberrations in the eye and provide image metrics derived from the measured aberration in the eye.

By design, conventional phoroptors in the prior art are not suited for astigmatism-free refractive corrections. An improved phoroptor must address the issues of relating the cylindrical axis of the phoroptor to the orientation of the eye in an objective refractor, and controlling cylindrical power in a resolution much finer than 0.25 D.

Figure 7:
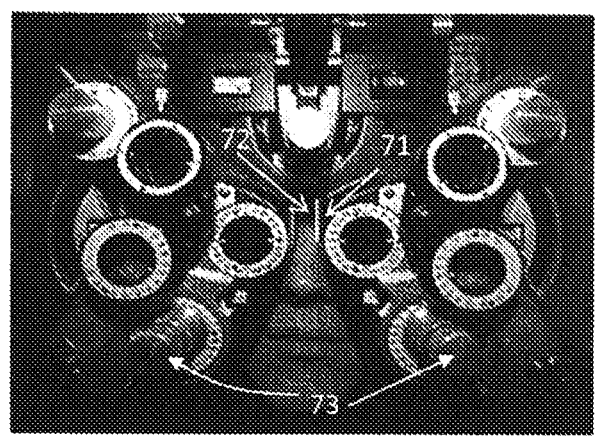
FIG. 7 shows a phoroptor for subjective refraction of an eye in accordance with an embodiment.
Figure 7:
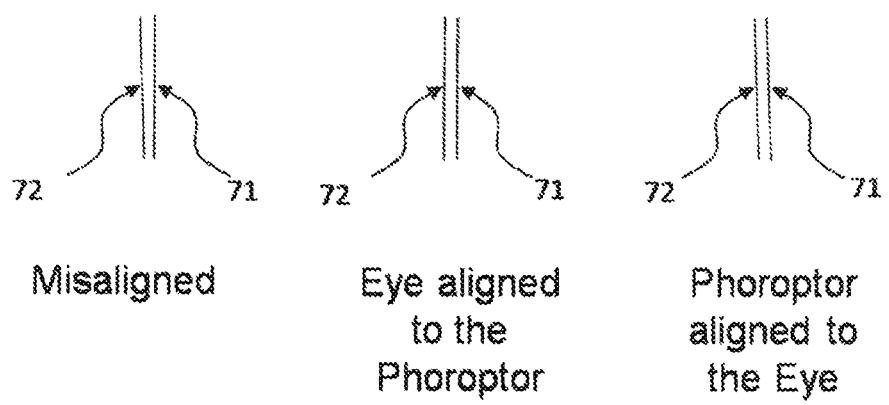

FIG. 7 shows an improved phoroptor for inclusion in the measuring station to allow for subjective refraction of an eye in accordance. A registration mark 72 is placed on face of a patient. An objective refraction of the eye can be obtained with its cylindrical axis relating to the alignment mark 72. When the same eye is placed behind a phoroptor, a light beam 71 from the phoroptor can be placed next to the registration mark for relating the cylindrical axis of the phoroptor to an orientation of the eye in another measurement.

Relating the cylindrical axis of a phoroptor to an orientation of an eye in an objective refractor may involve using the aid of a mechanical device, a light beam, a projected image, or an image device. Relating the cylindrical axis of a phoroptor to the cylindrical axis of an eye in an objective refractor may also involve comparing a fixed orientation such as an alignment mark 71 attached to a phoroptor to an orientation of an eye such as a registration mark 72 on the face of a patient or in an eye. Relating the cylindrical axis of a phoroptor to the cylindrical axis of an eye in an objective refractor may involve adjusting an orientation such as an alignment mark 71 attached to a phoroptor to match to an orientation of an eye specified by a registration mark 72 on the face of a patient or in an eye, and determining an angular offset from the adjustment to the alignment mark attached to the phoroptor.

The improved phoroptor associated with the measuring station further includes a digital control and display of its cylindrical axis instead of a manual control of the cylindrical axis 73. The digital control may be achieved using motorized control of the cylindrical axis.

The improved phoroptor can further include a mechanism for achieving cylinder correction continuously instead of every 0.25 D as in conventional phoroptors.

The improved phoroptor can further include a mechanism for achieving refractive correction of spherical aberrations in an eye using a plurality of phase plates or a plurality of lenses with aspheric surface profiles.

Figure 8:
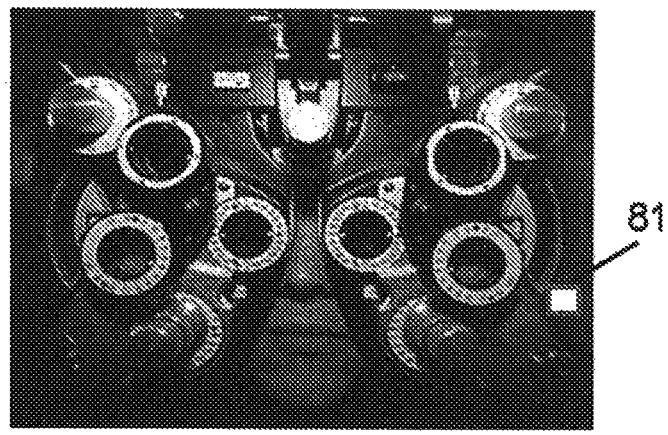
FIG. 8 shows another phoroptor for subjective refraction of an eye in accordance with an embodiment.

In another embodiment, an improved phoroptor for subjective refraction of an eye includes a mechanism for entering a cylindrical power and a cylindrical axis manually or for importing refractive data from an objective refractor for improved efficiency and accuracy. Such a phoroptor is illustrated in FIG. 8 and comprises: a) a plurality of spherical lenses for the correction of defocus in an eye; b) a plurality of cylindrical lenses for the correction of astigmatism in an eye; c) a mechanism 81 for importing refractive data from an objective refractor.

Improved Objective Refractors for Refractive Correction of an Eye

A conventional wavefront aberrometer determines cylindrical error with high accuracy, but is not sufficient for astigmatism-free refractive correction. This is because conventional wavefront aberrometers do not provide a reliable measurement of spherical focus power for setting an eye to its far accommodation point, and do not contain a mechanism to precisely link the cylindrical axis measured in an objective refractor to the cylindrical axis in a phoroptor for a subjective refraction or an ophthalmic lens.

Figure 9:
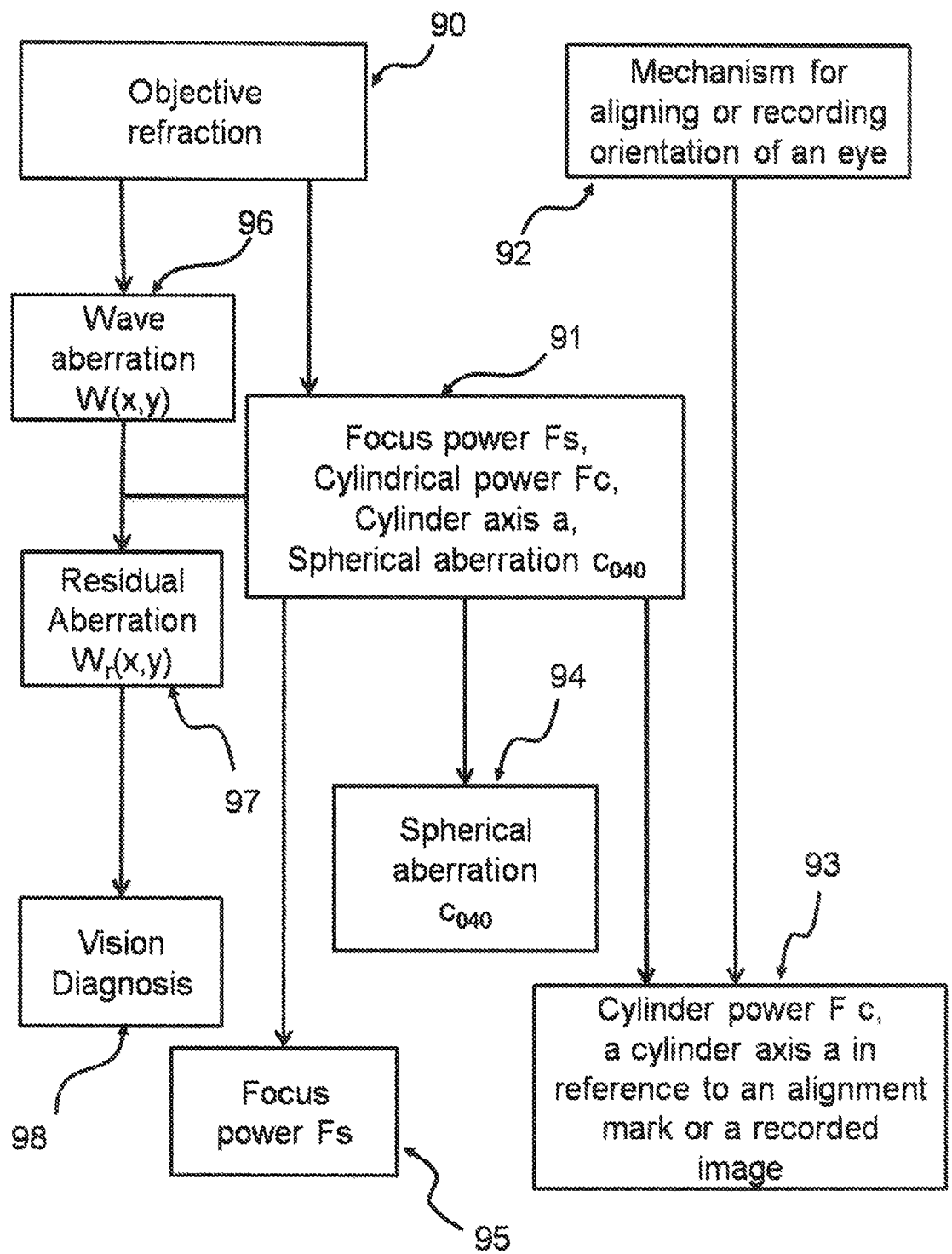
FIG. 9 shows a flow chart for an improved method for manifest refraction in accordance with an embodiment.

FIG. 9 shows an improved objective refractor system for a refractive correction. The system comprises an objective refraction device 90 for measuring refractive errors of an eye including at least a cylindrical power, a cylindrical axis, and a spherical focus error without any subjective response, and a mechanism for aligning orientation of an eye to a predetermined direction in the objective refractive device or for recording the facial orientation of an eye during an objective refraction 92.

In one embodiment, the objective refraction device 90 is an objective aberrometer that measures wavefront slopes across the pupil of an eye. The wavefront aberrometer provides at least a spherical focus power, a cylindrical power, a cylindrical axis, and an optional spherical aberration of an eye to storage element 91. The focus power and optional spherical aberration are available on output devices 95 and 94 respectively.

The mechanism for aligning or recording orientation of an eye 92 in one embodiment allows changing relative orientation of an eye to a predetermined direction in the objective refraction device, and provides a visual aid for setting up the relative orientation between the refraction device and the eye under test. In combination with the data in storage element 91, the objective refractor system is able to output a cylindrical power and cylindrical axis in reference to the alignment mark or recorded image in output device 93.

The mechanism for aligning or recording facial orientation of an eye 92 in one embodiment uses a digital camera to record at least a portion of a human face. The human face may include a computer-generated (via the measuring station) alignment mark, in the form of a frame for a spectacle lens without a refractive element.

In another embodiment, the objective refraction device can further provide total wave aberration of an eye 96, and vision diagnosis 98 based on the total wave aberration, data from a refractive correction, and a residual wave aberration 97, wherein the refractive correction includes a spherical focus power, a cylindrical power, a cylindrical axis, and an optional spherical aberration.

An Improved Manifest Refraction for Refractive Corrections

With the improved phoroptor and wavefront aberrometer provided as part of the measuring station according to the present disclosure, an improved method of manifest action for astigmatism-free customized refractive correction is provided. The method comprises of the following steps. First, an artificial registration mark is placed on a human face. Second, an objective estimation of the eye's focus error, cylindrical power, and cylindrical axis is obtained using an objective refractor. The focus power from the objective refraction has a resolution of 0.25 D and the cylindrical power has a resolution finer than 0.25 D, e.g. 0.10 D or 0.025 D. The objective refractor is preferably a wavefront aberrometer. Third, orientation information of an eye in reference to the objective refractor is stored based on the artificial mark placed on the face. Fourth, before performing subjective refraction with a phoroptor, the tested eye in a phoroptor is aligned or checked based on the stored orientation information of an eye. Fifth, the measuring station dials in a cylindrical correction matching the obtained cylindrical power and cylindrical axis from the objective refractor. Sixth, a plurality of spherical corrections in addition to the dialed-in cylindrical correction is presented to the patient by the station. A revised focus power is obtained as an improvement over the objectively measured focus error to offer an optimized correction of an eye for far vision. Seventh, refractive correction data for manufacture of an ophthalmic lens is generated by combining the objectively determined cylindrical refractive power and axis and the subjectively revised focus power.

Refraction Systems for Remote and Subjective Measurement of Human Eyes

Figure 10A:
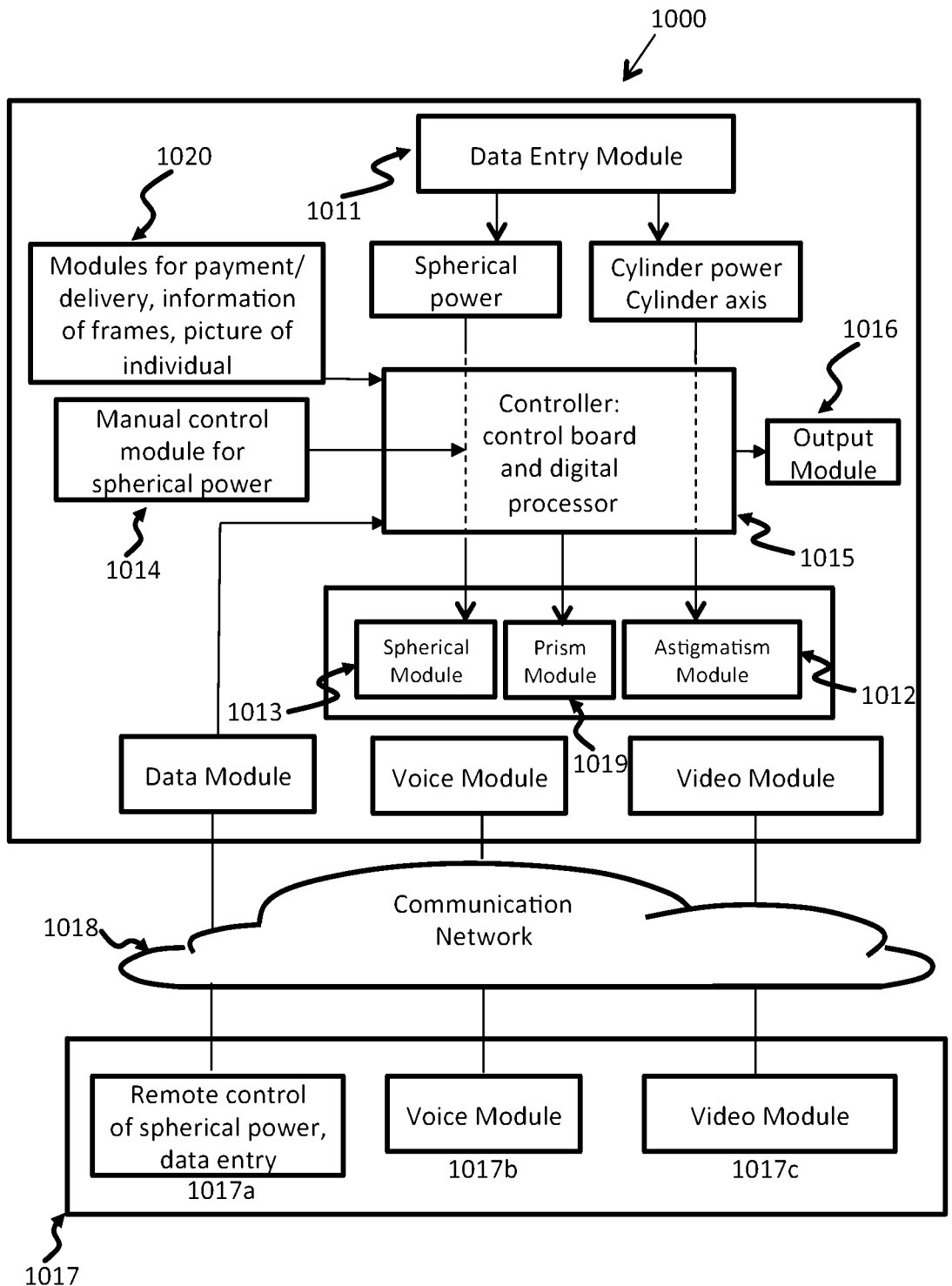
FIG. 10a shows a schematic diagram of an exemplary refraction system for determining a spherical power of an eye subjectively for prescription of eyeglasses.

FIG. 10a shows a schematic diagram of an exemplary subjective system 1000 for remote measurement of refractive errors in an eye. In one embodiment, the subjective system 1000 includes 1) a data entry module 1011 capable of obtaining a refractive data of an eye that include a spherical focus, an astigmatism having a cylinder power and a cylinder angle; 2) an astigmatism module 1012 configured for the correction of an astigmatism imported from the data entry module 1011; 3) a spherical module 1013 for providing a plurality of focus powers for the subjective determination of myopia, hyperopia and presbyopia; 4) a manual control module 1014 connected to the spherical module 1013 for the adjustment of the spherical module 1013, 5) a controller 1015 configured to enable the manual control module 1014 for manual and incremental adjustment of focus power and to enable the astigmatism module 1012 to dial-in imported astigmatism data automatically, where the controller 1015 includes a control board and a digital processor; 6) an output module 1016 configured to present a refractive prescription in the form of printing, displaying, or exporting; and 7) a module of remote control 1017 configured for controlling the refraction system at a location away from the system through a communication network connection 1018. In some embodiments, the manual control module 1014 is configured to be accessible to the patient for self-adjustment. The amount for incremental adjusting of focus power may be 0.25 D or 0.125 D, and the focus power can be increased or decreased.

Figure 10B:
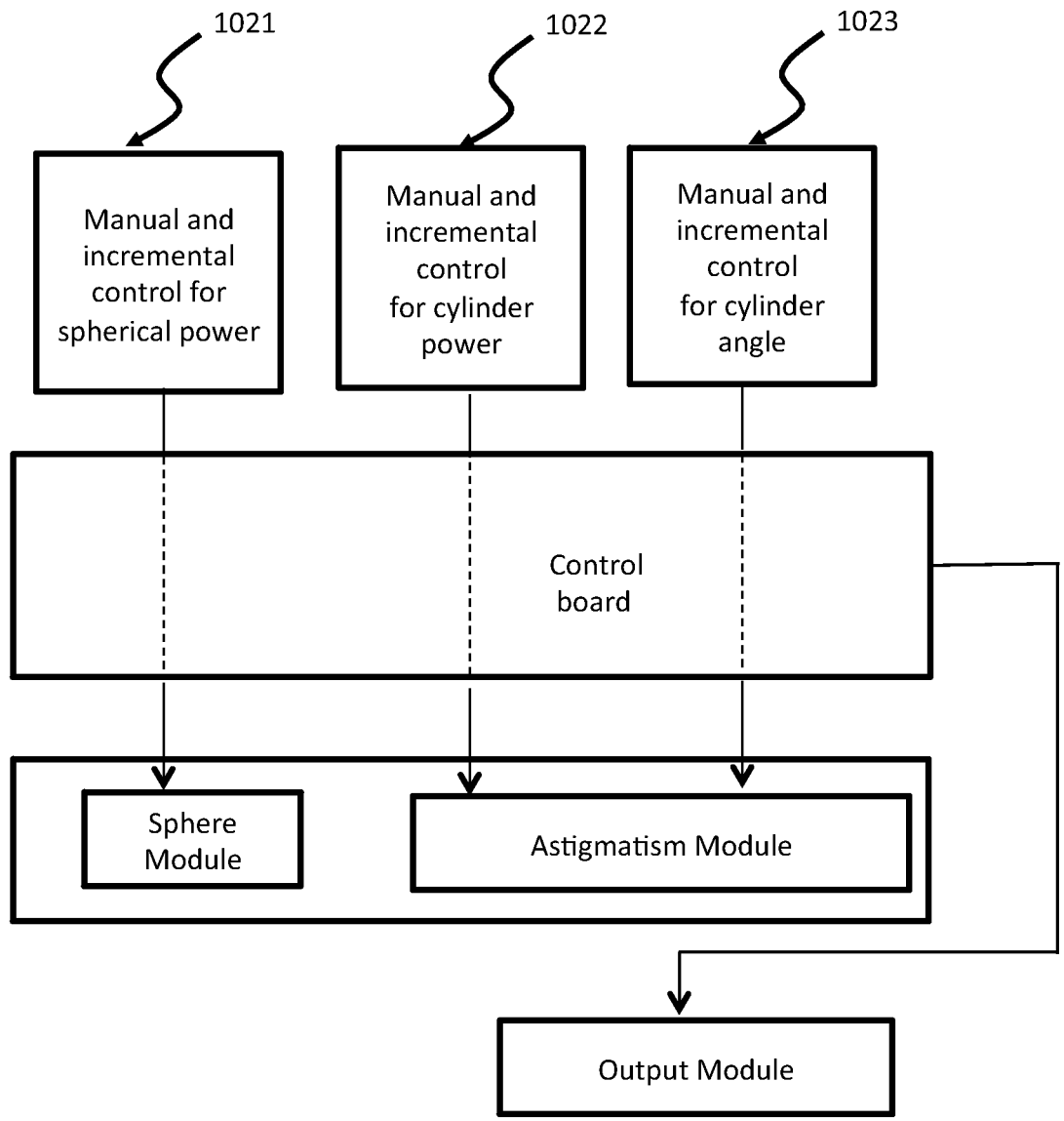
FIG. 10b shows a schematic diagram of a phoroptor as known in the art, for subjective determination of a focus power, a cylinder power, and a cylinder angle.

Unlike traditional phorophors, shown in FIG. 10b, that are designed for subjective optimization of all three independent parameters (a spherical power 1021, a cylinder power) 1022 and a cylinder angle 1023) by an examiner, the system in the present disclosure allows subjective optimization of spherical power only. Eliminating two out of three independent parameters in the subjective refraction process not only reduces examination time dramatically, but also makes the final prescription of eyeglasses unique and independent of the examiners. In traditional subjective refraction, because all three parameters have an impact on vision at the same time, there are many possible combinations of a focus power, a cylinder power, and a cylinder angle that can yield the same visual acuity. Therefore, skills and experience of the individual examiner determines the best corrected acuity and quality of vision for the patients.

The system in the present disclosure relies on knowing astigmatism in an eye before a subjective refraction. It is well-known that all aberrations in an eye, including astigmatism, spherical aberration and coma, can be determined objectively from a wavefront sensor for the eye. Astigmatism (cylinder power and cylinder axis) of an eye can be precisely determined by objectively optimizing retinal image quality of an eye from all the aberrations obtained from a wavefront measurement. In one aspect; the determination of astigmatism is objective and it does not depend on skills and experience of an examiner as well as not depending on the quality of patient feedback in the subjective refraction. In another aspect, the astigmatism obtained from a wavefront sensor may be far more accurate than those from a subjective refraction because the objective optimization is performed by a computer. In yet another aspect; accuracy in determining an eye's astigmatism from a wavefront sensor will be about 0.05 D, much finer an 0.25 D in subjective refraction. In still another aspect, further astigmatic correction, the data entry module in the present disclosure is no longer limited by the manual and incremental adjustment of 0.25 D with a conventional phoroptor in the prior art, and it allows importing cylinder power as fine as 0.01 D. Therefore, the precision and resolution of the cylinder correction in the present methods and systems will be much finer than that with conventional phoroptors.

The data entry module 1011 of FIG. 10a in one embodiment can be achieved with a manual importing device such as a keyboard, a mouse, a pointing device, or a touch screen. The data entry to the data entry module 1011 in other embodiments can also be achieved by reading an electronic file that contains refraction data of an eye from a storage device, a file in a remote computer system, or a file from a network connection. This file can also be obtained from a patient record of historical measurements, or obtained by measuring a pair of existing glasses with a lensometer as well.

Once astigmatism of an eye is precisely determined and entered in the system, the astigmatism module 1012 is configured such that manual and incremental adjustment to the cylindrical power and cylindrical angle for the combined lenses is excluded. This exclusion of cylindrical power and cylindrical angle is completely different from conventional phoroptors.

Because the subjective refraction system in the present disclosure provides fast, precise, and unique prescription of an eye, and it can be configured for remote measurement through a network such as the internet. The remote control system provides the following functionalities: 1) remote data entry, 2) remote adjustment of the spherical module 1013, and 3) remote voice/video communication between the patient at an examination location and the examiner away from the refraction system at the examination location. In one embodiment, the module of remote control 1017, connected to the refraction system through an electronic network 1018, includes at least one of i) a remote control of spherical power 1017a, which can include a data module for data entry and transfer, ii) a module for voice communication 1017b between the human subject and the examiner, and iii) a module for video communication 1017c for real-time monitoring of the refraction process or for communication between the patient and the examiner.

In yet another aspect, differing from traditional phoroptors, the refractive prescription from the subjective system in the present disclosure includes a spherical power based on subjective response for different settings of lenses in the spherical module, and a cylinder power and a cylinder angle that is not optimized by subjective refraction.

The subjective system in the present disclosure can be further configured such that the astigmatism module 1012 includes two independent astigmatism modules, and the spherical module 1013 includes two independent spherical modules, for testing two eyes of the human subject. The subjective system can also include a prism module 1019 for the measurement of prism offsets between two eyes.

In one aspect, the subjective system in the present disclosure is further configured with a transportation system for mobile operation. The transportation system may be, for example, a van or vehicle large enough for setting-up refraction related systems and devices.

In another aspect, the subjective system in the present disclosure can be further configured with one or more input modules 1020 to accept payment information and delivery information from an individual, and/or to receive information of frames for eyeglasses or sunglasses input module 1020 may also be configured as a camera to take a picture of the human subject with or without the selected frames.

Refraction Systems for Remote and Objective Measurement of Human Eyes

A wavefront sensor for human eyes measures all aberrations in the eye without any subjective feedback from patients or subjective intervention from an examiner, and is therefore an objective system. In the present disclosure, a wavefront sensor for remote measurement of human eyes for the prescription of eyeglasses and sunglasses is described.

FIG. 1a shows a schematic diagram of an exemplary objective system 1100 for remote measurement of refractive error in the eye according to some embodiments. The system 1100 includes 1) a light source 1121 configured to produce a compact image at a retina of an eye; 2) an optical relay 1122 that reproduces a wavefront emerging from the eye due to reflected light from the retina to a measurement plane away from the eye; 3) a wavefront sensor 1123 at the measurement plane, including a wavefront sampling device and a digital image module or device, to record images of a wavefront that passes through the wavefront sampling device; 4) a digital processor 1124 configured to take a sequence of wavefront measurements at one time; 5) a display module 1125 for displaying wavefront images with automatic detections of sampling points of the wavefront sampling device in wavefront sensor 1123, 6) a real-time measurement intervention module 1126 for accepting or rejecting one or more wavefront measurement(s); 7) a data consolidation module 1127 for calculating a spherical power and an astigmatism (cylinder power and cylinder angle) based on a statistical analysis from a plurality of accepted measurements; 8) an output module 1128 configured to communicate a refractive prescription, including a focus power, a cylinder power and a cylinder angle; 9) a module of remote control 1129 that allows the wavefront system 1100 to be operated by an examiner at a location away from the wavefront system; and 10) a module for eye positioning 1130 with motion control.

It is well known that aberrations in human eyes are not static and change from moment to moment due to changes in tear film, variation in pupil sizes, and micro-fluctuation of accommodation. For prescription of eyeglasses, one set of focus power, cylinder power and cylinder angle is provided based on a number of wavefront measurements of the eye over a period of time. Differing from conventional wavefront sensors for the eye in the prior art, which is also known as an aberrometer 1150 as shown in FIG. 11b, the wavefront sensor in the present disclosure is designed specifically for the prescription of eyeglasses.

TABLE 1

Comparison of wavefront systems for the eye

| | Wavefront sensor (Conventional) | Wavefront sensor of the present disclosure |
|---|---|---|
| Objective | All aberrations in an eye | Data for eyeglasses prescription only |
| Measurement Required | One measurement at a time | A plurality of measurements for changes in aberrations over time |
| Real-time data validation | No, each measurement by itself is an event | Yes, bad measurements are excluded for the prescription of eyeglasses |
| Real-time data consolidation | No | Yes, consolidation from a plurality of measurements is required |
| Data output | One measurement of all aberrations including spherical power, astigmatism, spherical aberration, coma, etc. | Consolidated data for a prescription of eyeglasses: spherical power, and astigmatism only for prescription of eyeglasses |

Table 1 shows fundamental differences between aberrometers known in the art and the present wavefront refraction system. For obtaining one set of refraction data for eyeglasses, a plurality of measurements of the aberrations in an eye is taken at one time such as over several seconds. Data validation is performed by accepting good measurements and eliminating poor measurements that can be seen from the wavefront images along with the analysis results. The refraction data for each accepted measurement is determined, and produces a consolidated refraction data of a spherical power and an a stigmatism (a cylinder power and a cylinder angle) from a plurality of accepted measurements. Differing from the conventional wavefront sensor known in the art, the output of the present wavefront refraction system for eyeglasses contains only a spherical power and an astigmatism having a cylinder power and a cylinder axis.

In one embodiment, the wavefront system 1100 is configured to take a sequence of wavefront measurements at one time, which involves a) storing a plurality of wavefront images of the wavefront sensor into a memory unit, b) providing automatic detections of sampling points of the wavefront sensor, c) calculating wavefront slopes across a pupil of the eye, and d) determining wave aberration of the eye that includes at least a focus error, an astigmatism, and a spherical aberration, and e) displaying wavefront images (e.g., display module 1125) with automatic detections of sampling points of the wavefront sensor. The steps (b)-(d) (i.e., providing, calculating and determining) may be performed by digital processor 1124. The real-time measurement intervention module 1126 in the present system is configured to allow an examiner or other qualified optical professional to validate and accept a plurality of wavefront measurements. In one embodiment, the real-time measurement intervention module 1126 comprises a pointing device enable the examiner to submit input for rejecting an invalid measurement in a sequence of wavefront measurements due to errors in automatic identification of image analysis, ii) inadequate pupil size for wavefront measurements, and iii) poor image quality of the wavefront sensor due to tear films or blinking eyes. The data consolidation module 1127 is configured for calculating a spherical power and an astigmatism (cylinder power and cylinder angle) based on a statistical analysis from the accepted measurements provided through the measurement intervention module 1126.

Different from aberrometers in the prior art, the wavefront system in the present disclosure is further configured for remote operation so that the wavefront system can be operated by an examiner at a location away from the wavefront system. The remote control module 1129 is used for i) data communication between the digital processor 1124 for the wavefront sensor 1123 and a control system 1131 away from the wavefront system 1100, and ii) remote voice 1132/video 1133 communication between the patient at an examination location and the examiner away from the wavefront sensor 1123. In one embodiment, the module of remote control 1129, connected to the wavefront sensor 1123 through an electronic network 1134, comprises at least one of 1) a data module 1131 for data entry and transfer, 2) a module for voice communication 1132 between the human subject and an examiner, and 3) a video module 1133 for real-time monitoring of the refraction process or for communication between the patient and an examiner.

The wavefront system in the present disclosure is further configured to include a module for motorized eye positioning system 1130. In one embodiment, the motorized eye positioning system includes a head rest, a motion control system for positioning the head rest at a plurality of positions, a camera system for real-time monitoring of the position of the eye, and a motion control system controlled by the digital computer 1124. In some embodiments, the camera system monitors the relative position between the eye and an optical axis of the system.

The output module 1128 of the wavefront system may be further configured to include a data communication module for transferring a refractive prescription in the form of printing, displaying, or exporting. In one embodiment, the data communication includes at least one of: a) generating a file of the prescription in a storage device, b) sending a file of the prescription through a network communication to another device, and c) communicating refraction data and, in some embodiments, patient information to a phoroptor.

In yet another embodiment, the wavefront sensor can be generalized to any objective refraction device that generates objective measurement of a focus power, and an astigmatism having cylinder power and a cylinder angle.

Figure 12:
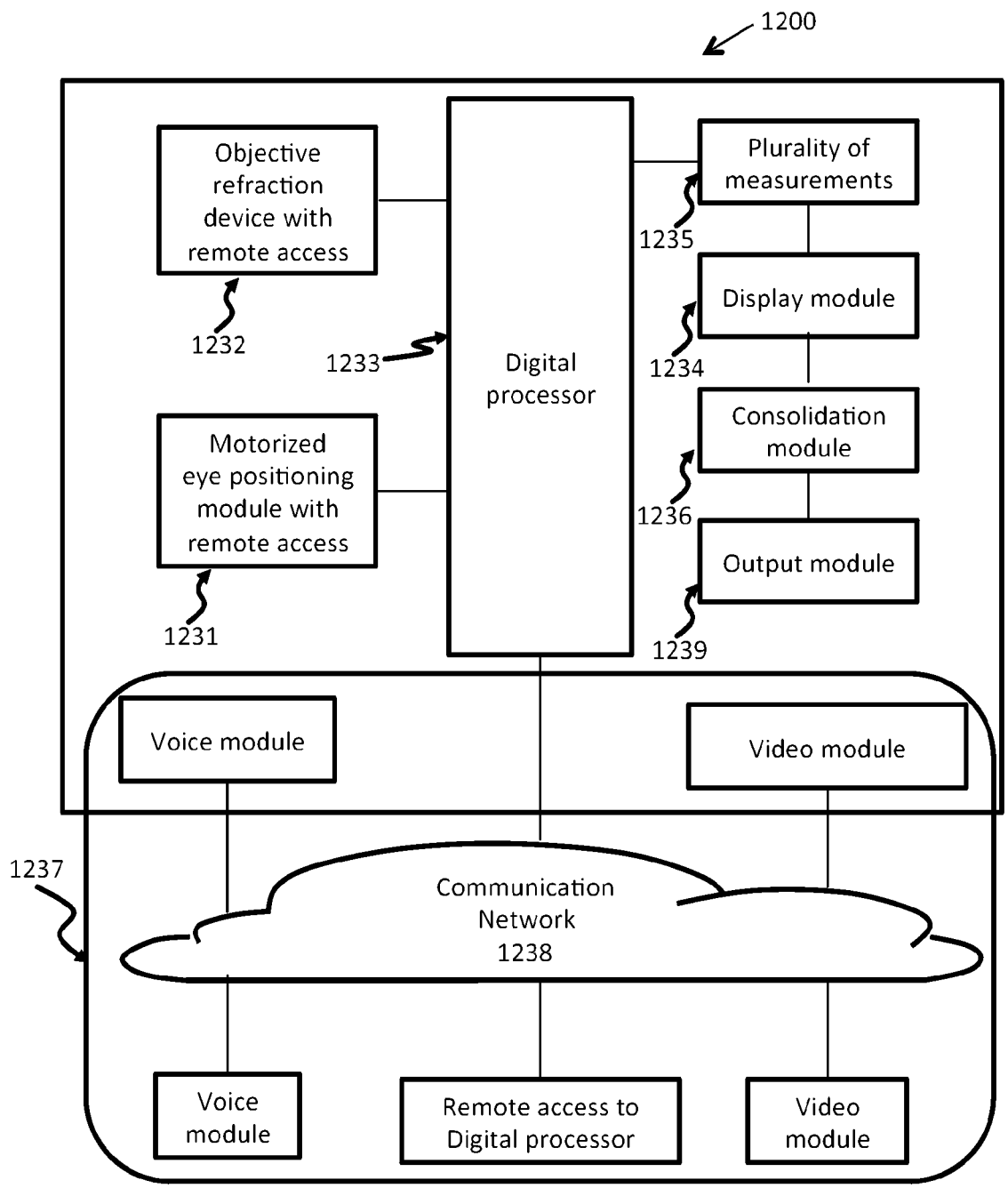
FIG. 12 shows an exemplary schematic diagram of a refraction system for remote measurement of refractive errors in human eyes.

FIG. 12 shows a schematic diagram for such a generalized system 1200 according to an embodiment. System 1200 includes 1) a module for motion-controlled (e.g., motorized) eye positioning 1231 that may include a head rest, a motion control system for positioning the head rest at a plurality of positions, and a camera system for real-time monitoring of the relative position between the eye and an optical axis of the refraction system; 2) an objective refraction device 1232 for measuring refractive errors of an eye that includes a cylinder power, a cylinder angle, and a spherical power; 3) a digital processor 1233 configured for the control of eye positioning module 1231 and the objective refraction device 1232, 4) a display module 1234 for displaying results of a plurality of measurements 1235; 5) a data consolidation module 1236 for generating one set of refraction data that includes a spherical power, and an astigmatism having a cylinder power and a cylinder angle; 6) a module of remote control 1237 for an examiner to remotely control the digital processor 1233 away from the refraction system, which is connected to the refraction system through an electronic network 1238; and 7) an output module 1239 configured to present a refractive prescription in the form of printing, displaying, or exporting. The objective refraction device 1232 and motorized eye positioning device 1231 have remote access by the module of remote control 1237.

Integrated Systems for Remote Measurement of Refractive Errors in Human Eyes

Figure 11A:
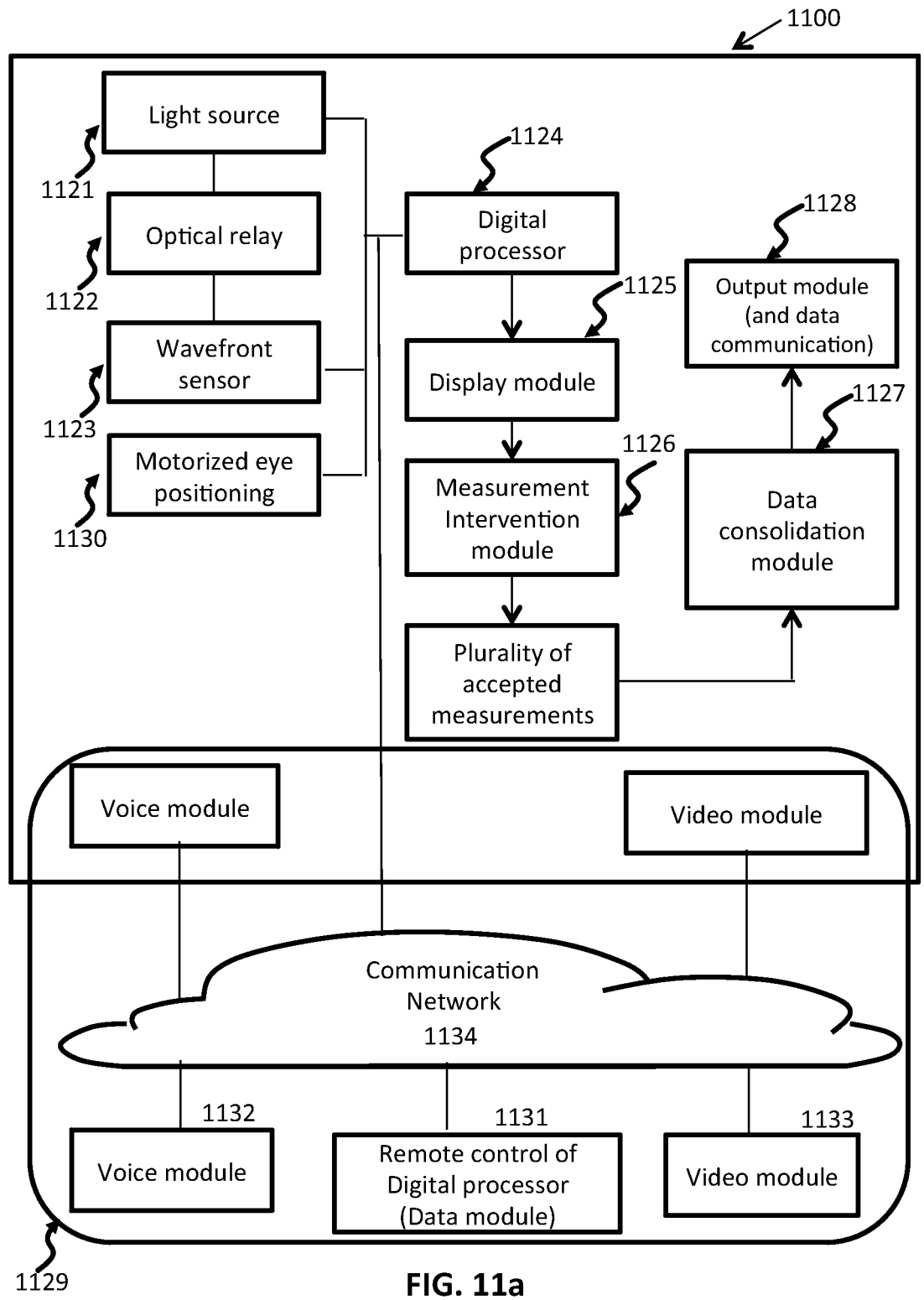
FIG. 11a shows a schematic diagram of a wavefront system of an eye for prescription of eyeglasses in one embodiment.
Figure 11B:
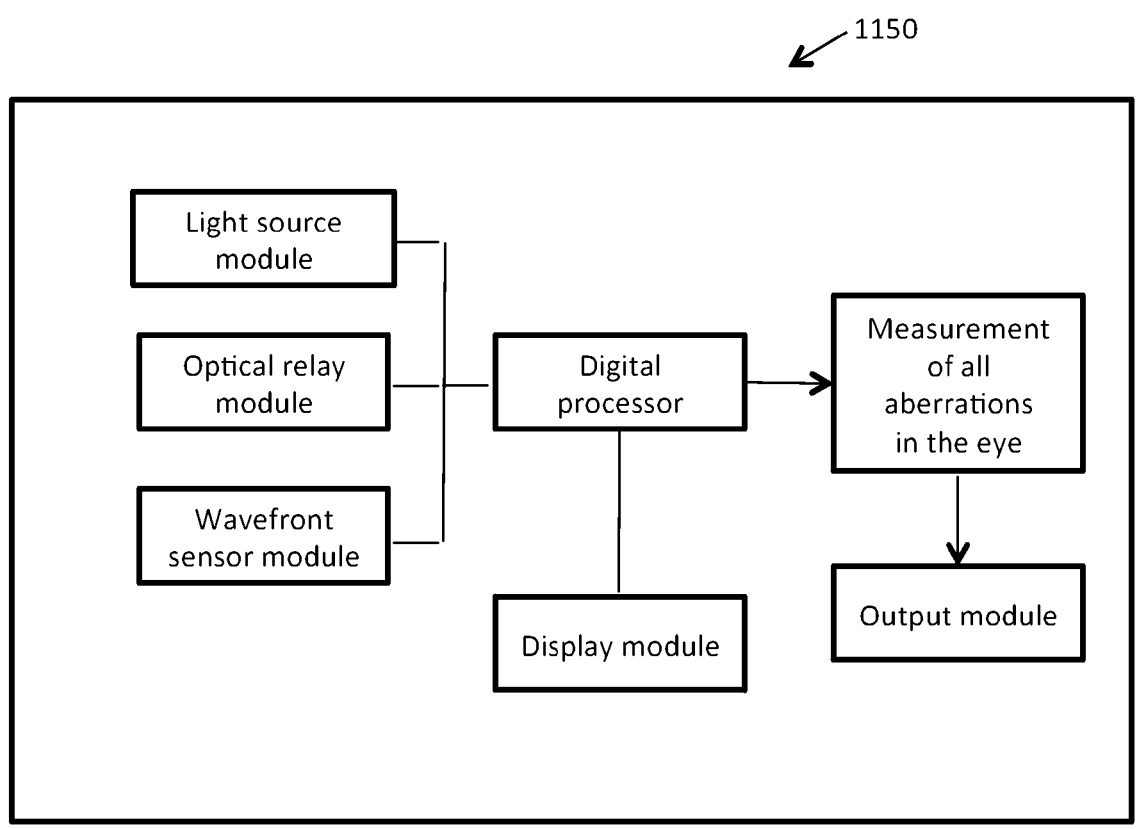
FIG. 11b shows a schematic diagram of a conventional wavefront system of an eye, which is also called aberrometer.
Figure 13:
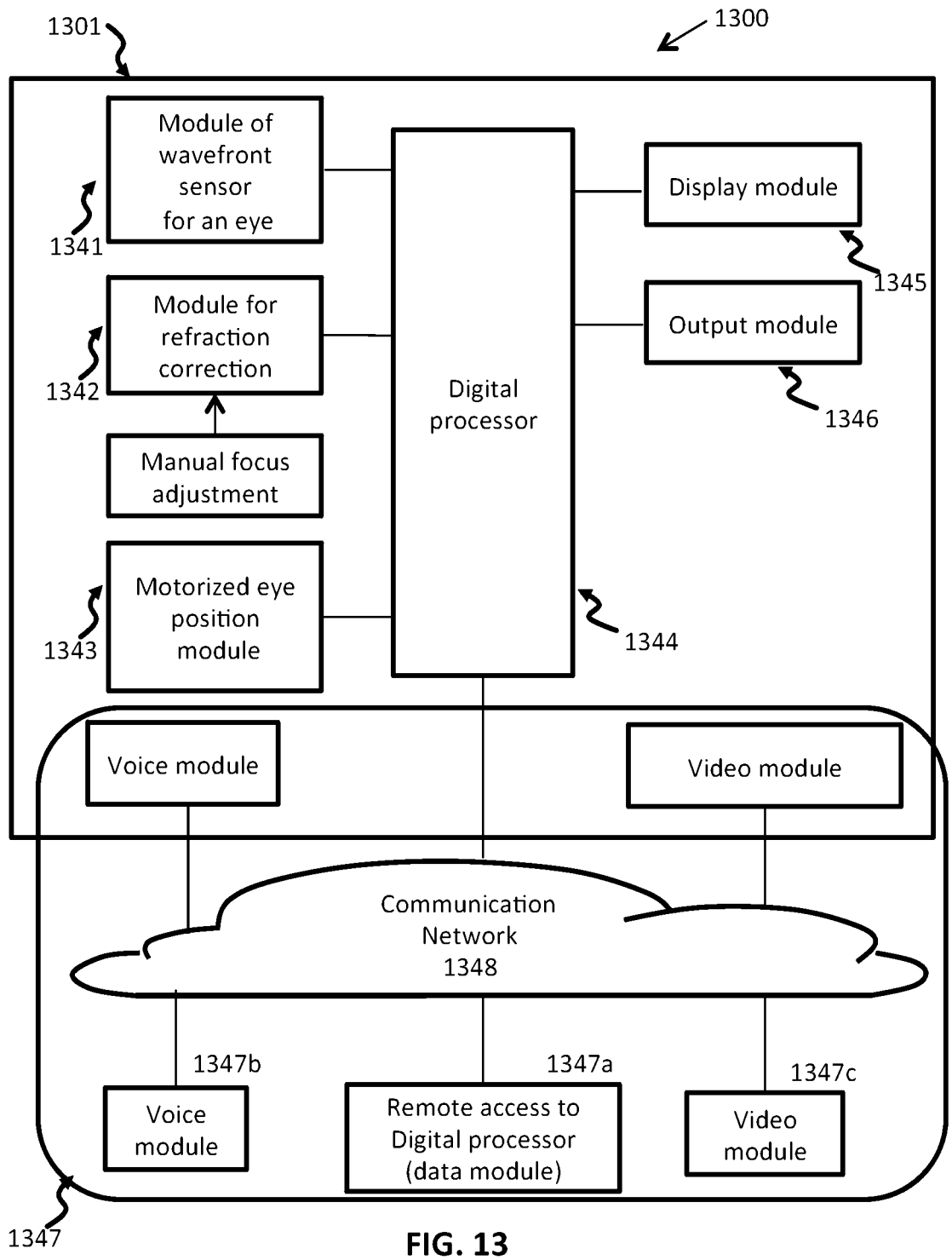
FIG. 13 shows a schematic diagram of an integrated refraction system for remote measurement of refractive errors in human eyes, in one embodiment.

Combining the objective systems in FIG. 11a or FIG. 12 with the subjective system in FIG. 10a will produce a more effective integrated system for remote measurement of refractive errors in the human eye. FIG. 13 shows a exemplary schematic diagram of such an integrated system 1300.

The integrated system 1300 includes: 1) a wavefront sensor module 1341 for the eye for objective measurement of the eye's refractive errors; 2) a refraction correction module 1342 for the correction of determined astigmatism from the wavefront sensor module 1341 and subjective determination of a spherical power; 3) a module for motorized eye positioning 1343 that includes a head rest, a motion control system for positioning the head rest at a plurality of positions, and a camera system for real-time monitoring of eye position; 4) a digital processor 1344 configured for the control of the refraction correction module 1342, the head position module 1343, and the wavefront sensor module 1341; 5) a display module 1345 for the digital processor 1344; 6) an output module 1346 configured to present a refractive prescription in the form of printing, displaying, or exporting; and 7) a module of remote control 1347 for an examiner to remotely control the digital computer away from the refraction system. The module of remote control 1347 is connected to the refraction system 1301 through an electronic network 1348 and includes at least one of i) remote access 1347a for the digital processor 1344, including a data module for data entry and transfer, ii) a module for voice communication 1347b between the human subject and an examiner, and iii) a video module 1347c for real-time monitoring of the refraction process or for communication between the patient and an examiner.

In one embodiment, wavefront sensor module 1341 includes 1) a light source configured to produce a compact image at a retina of an eye; 2) an optical relay that reproduces a wavefront emerging from the eye due to reflected light from the retina to a measurement plane away from the eye; and 3) a wavefront sensor at the measurement plane, including a wavefront sampling device and a digital image module, to record images of a wavefront that passes through the wavefront sampling device. Digital processor 1344 performs data analysis for wavefront sensor 1341. In some embodiments, the light source is configured to produce a compact image at the retina, where reflected light from the retina generates an outgoing wavefront in front of a cornea of the eye from a reflection of the retina.

The digital processor 1344 takes a sequence of wavefront measurements at one time, which involves a) storing multiple wavefront images into a memory unit, b) providing automatic detections of sampling points of the wavefront sensor, c) calculating wavefront slopes across a pupil of the eye, and d) determining a wave aberration of the eye that includes at least a focus error, an astigmatism, and a spherical aberration.

The refraction correction module 1342 includes an astigmatism module and a spherical module. The astigmatism module is configured such that manual and incremental adjustment to the astigmatism module is excluded and an astigmatic correction, including both cylinder power and cylinder angle is automatically controlled based on the obtained objective measurement from each eye of the individual. The spherical module of refraction correction module 1342 is configured for manual and incremental adjustment for the spherical power of the refraction correction module. In some embodiments, selection and arrangement of cylindrical lenses are determined by the astigmatism obtained from the digital processor/computer and the wavefront sensor.

E-Commerce Methods for Delivering Eyeglasses Over the Internet

In today's eyeglass industry, at least one optometrist in the United States or one optician in some country is needed in one store location even though about 3 pairs of eyeglasses are sold in each store location on average. This leads to many problems for the eyeglass industry. First, having one examiner—that is, an optometrist or optician—in one store is ineffective and expensive for a business because the optometrist or optician may not perform any eye examination if no eyeglasses are sold in a particular day. Second, the skills and experience of the optometrists (opticians) differ from person to person. People will get a poor vision correction if their eyes are examined by a low-quality optometrist. For eyes in complicated scenarios, having one optometrist in one store makes it difficult to get a second opinion if the optometrist is not experienced or skilled. Third, for a franchise store of eyeglasses, there is no uniform control of quality because refraction of human eyes is empirical and examiner-dependent, and cannot be quantitatively standardized.

These problems lead to expensive eyeglasses, such as about US$200 to $700 for a pair of single vision eyeglasses and US$400 to $1000 for progressive eyeglasses, and many unsatisfied customers with new eyeglasses.

To address issues of inefficiency and poor quality of vision correction, an e-commerce system and method is described for delivering eyeglasses in the present disclosure. First, in FIG. 14, measuring stations 1451, which are configured for remote measurement of refractive errors of eyes of an individual, are placed in shops spread in different geographic locations. In some embodiments there may be one measuring station 1451 in a single location, while in other embodiments, there may be more than one measuring station 1451 in various geographic locations. These measuring stations 1451 are connected to a network 1455 such as an internet connection. Second, one or more qualified examiner(s) are organized in a centralized refraction center 1452 away from the measuring stations at shops, and the examiners perform measurement of refractive errors in eyes of an individual. One examiner can operate measurement stations in a number of stores, and many examiners can contribute for determining prescription data for one patient in complicated situations. Third, correction data are generated and transmitted through the network 1455 to a manufacturing center or facility 1453. In some embodiments the manufacturing center 1453 may be a centralized facility, while in other embodiments the manufacturing center 1453 can include more than one facility. The correction data include an astigmatism having a cylinder power and a cylinder angle, and a spherical power, and they can further include the pupil distance between two eyes of an individual, data of frames for the eyeglasses 1454 (i.e., a digital system for eyeglass frames), and delivery information of the eyeglass shops and of the individual patient. Fourth, a pair of eyeglasses is manufactured and assembled in the manufacturing facility 1453 based on the transmitted data. Fifth, manufactured eyeglasses are delivered from the manufacturing center 1453 to the individual or eyeglass shops 1451 based on delivery information received from the network 1455.

The e-commerce approach has many advantages. First, it solves the problem of inefficiency because one optical examiner (e.g., optometrist or optician) in the central examination center 1452 can operate refraction systems in a number of stores. Second, it solves the problem of uniform quality control because the refraction data is not generated by one examiner in an local store, but rather by examiners in a centralized facility under strict rules for process control. Expert opinions in a complicated scenario can be formed by a group of optometrists in one centralized facility. By solving the inequality problem from store to store, one can build a franchise business for eyeglasses much more effectively. Third, this e-commerce approach paves the way for on-line based business because all data are digitally processed and digital custom eyeglasses can be delivered to customer at low cost. Finally, improving efficiency and custom satisfaction using the present methods can lead to better and less expensive eyeglasses.

The measuring stations for remote measurement of refractive errors of eyes of an individual are configured to: 1) obtain an objective measurement of refractive errors of each eye of the individual with an objective device like the one described in FIG. 11*a*, 2) determine a spherical power of an eye using a subjective system like the one described in FIG. 10*a*, 3) generate a refractive correction based on the astigmatism from the objective measurement, and the spherical power from the subjective system, and 4) provide communication between examiners and patients based on voice and video communication through an electronic connection. For example, an objective refraction device may include an interface configured to be coupled to a phoroptor for the subjective determination of a spherical power of an eye. In some embodiments, a focus power of each eye may be determined through subjective refraction, wherein the subjective refraction involves subjective responses in reading the acuity chart from the individual to a plurality of focus powers or a subjective decision made by the examiner based on network communication between the examiner and the individual.

In some embodiments, the remote measuring stations can be one or a combination of the systems shown in FIG. 10*a*, FIG. 11*a*, FIG. 12, FIG. 13 and FIG. 14.

In one embodiment, the personnel in the eyeglass shops according to the present disclosure are not examiners qualified or certified for eye refraction according to the laws or the regulations—that is, they are uncertified as examiners for eye refraction. Instead, the personnel are responsible for helping customers for the frame selection, accepting payment information from the individual, recording delivery information from the individual, and taking measurements such as pupil distance and pupil positions within a selected frame.

In one embodiment, the remote measuring stations further include selection of a frame for eyeglasses from an electronic system connected to the network, where selection of a frame involves a camera or digital imaging system used for taking a picture of an individual. Thus, the digital imaging system enables the individual to view an image of themself with and/or without the selected eyeglass or sunglass frames.

In yet another embodiment, an e-commerce method for delivering eyeglasses is configured for a franchise business, where all eyeglasses shops in different geographic locations use one standardized protocol for measuring human eyes, generating prescription data, manufacturing lenses, mounting lenses into frames, and delivering eyeglasses to customers.

Figure 14:
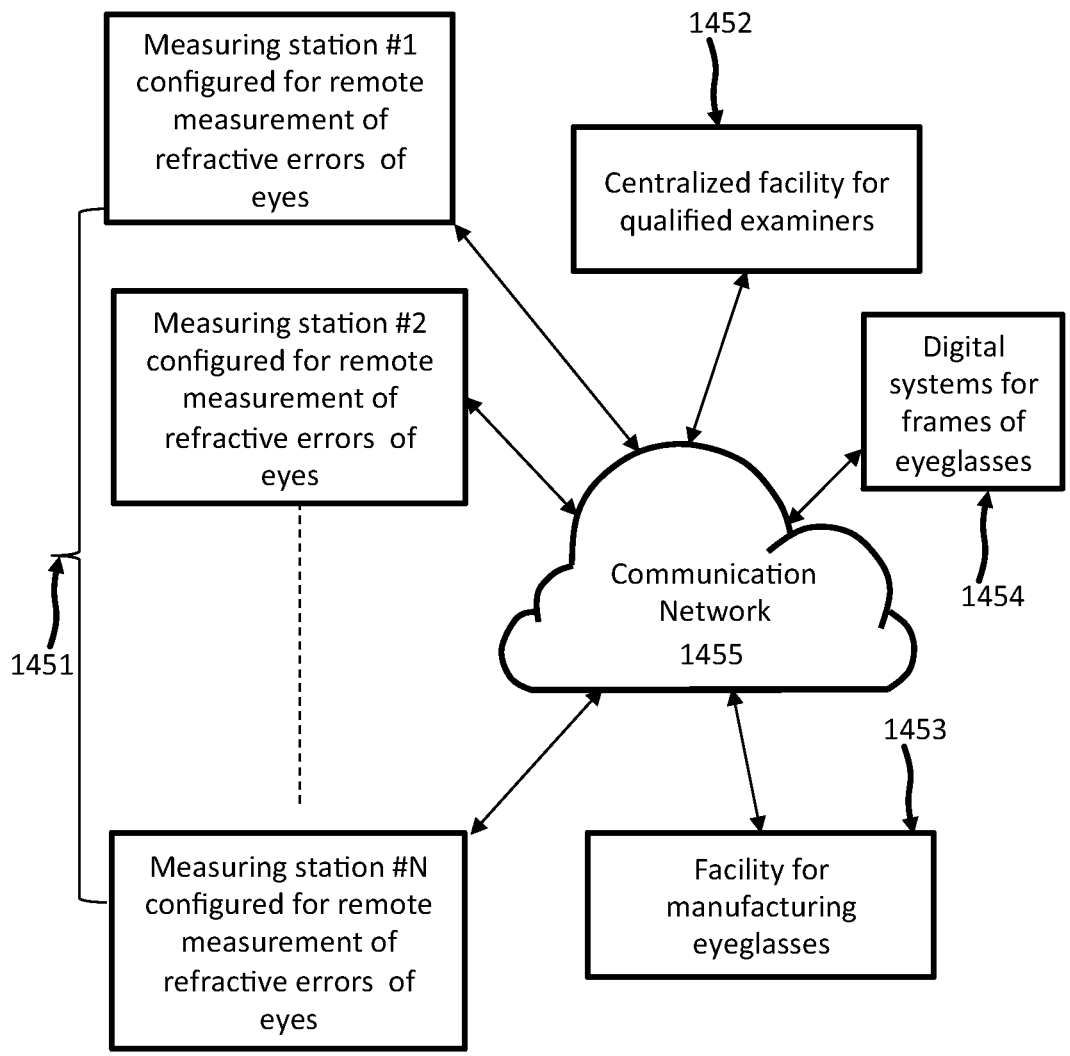
FIG. 14 shows a system for an electronic commerce method of measuring refractive errors of an eye and delivering customized eyeglasses, in one embodiment.
Figure 15:
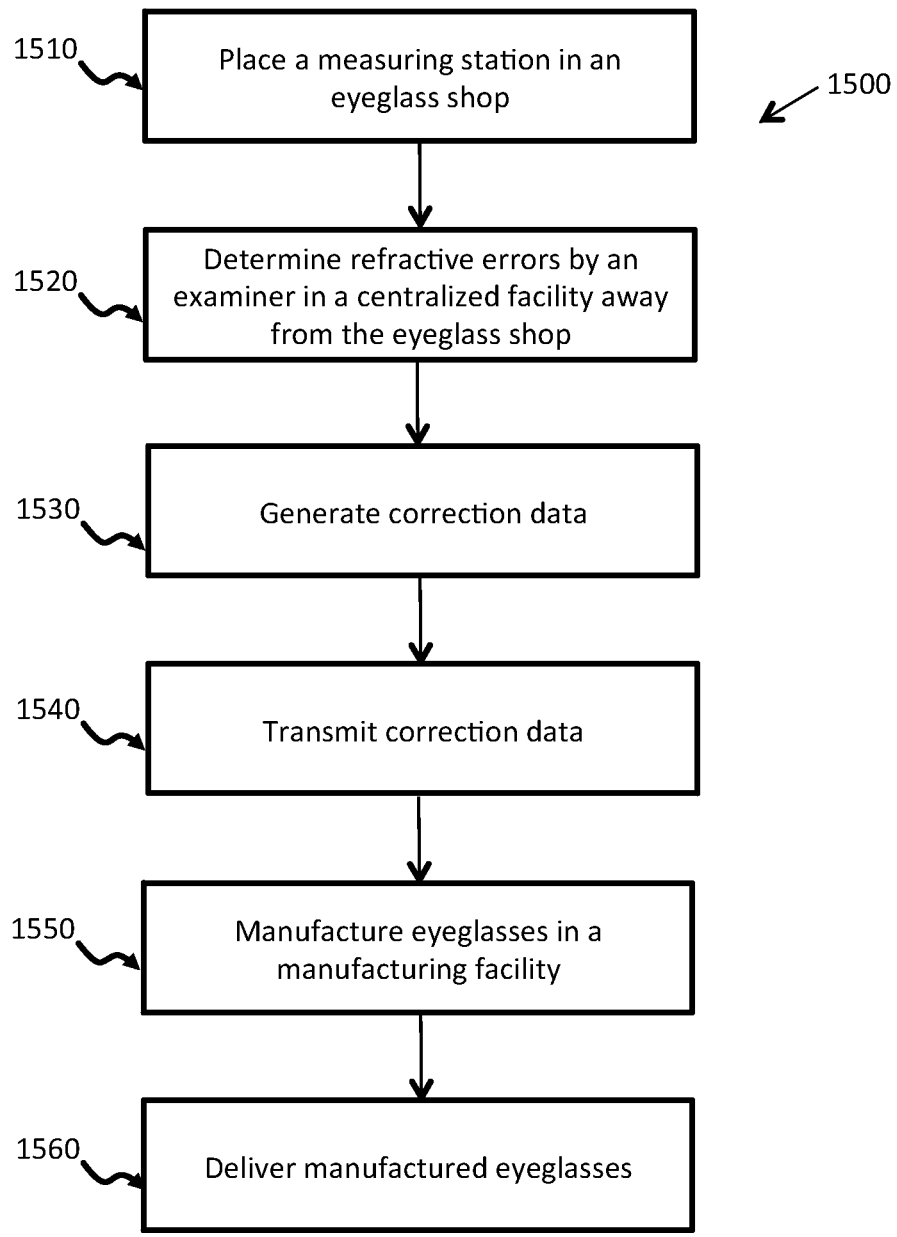
FIG. 15 shows a flowchart of an exemplary electronic commerce method for the system of FIG. 14.

FIG. 15 illustrates a flowchart 1500 of an exemplary embodiment of an electronic Commerce method for the system of FIG. 14. In step 1510, a measuring station for remote measurement of refractive errors of eyes of an individual is placed in a first eyeglass shop in a first geographic location, where the measuring station is connected to a network. In some embodiments, there may be a plurality of measuring stations placed in eyeglass shops that are in different geographic locations from each other. In step 1520, refractive errors in the eyes of the individual are determined by an examiner in a centralized facility away from the first eyeglass shop through the network, where the examiner is a certified optical examiner according to laws or regulations. In step 1530, correction data for making a pair of eyeglasses is generated, where the correction data is based on the refractive errors, the correction data including a spherical power, and an astigmatism having a cylinder power and a cylinder angle. The correction data can further include one or more of: a pupil distance between the eyes of the individual, data about frames for the eyeglasses, and delivery information of the eyeglass shops and/of the individual. In step 1540, the correction data is transmitted through the network. In step 1550, the pair of eyeglasses is manufactured in a manufacturing facility, the manufacturing being based on the correction data transmitted through the network. In step 1560, the manufactured eyeglasses are delivered to the individual or to the eyeglass shop based on delivery information received from the network.

While the specification has been described in detail with respect to specific embodiments, it will be appreciated that those skilled in the art, upon attaining an understanding of the foregoing, may readily conceive of alterations to, variations of and equivalents to these embodiments. These and other modifications and variations may be practiced by those skilled in the art, without departing from the scope of the present disclosure, which is more particularly set forth in the appended claims. Furthermore, those skilled in the art will appreciate that the foregoing description is by way of example only, and is not intended to limit the disclosure.

What is claimed is:

1. A wavefront system for measuring refractive errors of an eye for prescription of eyeglasses, comprising:
   a light source configured to produce a compact image at a retina of an eye, wherein reflected light from the retina generates an outgoing wavefront in front of a cornea of the eye from a reflection of the retina;
   an optical relay for reproducing a wavefront emerging from the eye at a measurement plane away from the eye;
   a wavefront sensor at the measurement plane, wherein the wavefront sensor includes a wavefront sampling device and a digital image module, the digital image module configured to record images of a wavefront that passes through the wavefront sampling device;
   a digital processor configured to take a sequence of wavefront measurements at one time, including a) storing a plurality of wavefront images of the wavefront sensor into a memory unit, b) providing automatic detections of sampling points of the wavefront sensor, c) calculating wavefront slopes across a pupil of the eye, and d) determining wave aberration of the eye that includes at least a focus error, an astigmatism, and a spherical aberration;
   a display module for displaying the wavefront images with automatic detections of sampling points of the wavefront sensor;
   a real-time measurement intervention module configured to i) validate and accept measurements from the sequence of wavefront measurements, wherein the measurement validation comprises displaying analyzed wavefront images on a display and rejecting invalid measurements in the sequence of wavefront measurements;

a data consolidation module for calculating a spherical power and an astigmatism based on a statistical analysis from the accepted measurements from the sequence of wavefront measurements, the astigmatism comprising a cylinder power and cylinder angle; and an output module configured to communicate a refractive prescription, wherein the refractive prescription includes at least a focus power, the cylinder power and the cylinder angle.

2. The wavefront system of claim 1 wherein the real-time measurement intervention module comprises a pointing device for rejecting an invalid measurement due to i) errors in automatic identification of image analysis, ii) inadequate pupil size for wavefront measurements, and iii) poor image quality of the wavefront sensor due to tear films or blinking eyes.

3. The wavefront system of claim 1 further comprising a module of remote control so that the wavefront system can be operated by an examiner at a location away from the wavefront system for at least one of i) data transfer between the digital processor in the wavefront sensor and the module of remote control, and ii) remote voice or video communication between the patient at an examination location and the examiner away from the wavefront sensor;

wherein the module of remote control is connected to the wavefront sensor through an electronic network, the module of remote control comprising at least one of i) a data module for data entry and transfer, ii) a module for voice communication between the patient and the examiner, and iii) a video module for real-time monitoring of the refraction process or for communication between the patient and the examiner.

4. The wavefront system of claim 1 further comprising a module for eye positioning, the module for eye positioning comprising:

a head rest;

a motion control system for positioning the head rest at a plurality of positions; and a camera system for real-time monitoring of the relative position between the eye and an optical axis of the wavefront sensor, wherein the motion control system is controlled by the digital processor.

5. The wavefront system of claim 1 wherein the communication of the refractive prescription is in the form of printing, displaying, or exporting.

6. The wavefront system of claim 5, wherein the communication of the refractive prescription comprises at least one of: a) generating a file of the prescription in a storage device, b) sending the file of the prescription through a network communication to another device, and c) communicating the refraction data to a phoroptor, wherein the file of the prescription may further include patient information.

* * * * *